(12) United States Patent
Mahadevan-Jansen et al.

(10) Patent No.: US 9,687,190 B2
(45) Date of Patent: Jun. 27, 2017

(54) INTRA-OPERATIVE USE OF FLUORESCENCE SPECTROSCOPY AND APPLICATIONS OF SAME

(75) Inventors: Anita Mahadevan-Jansen, Nashville, TN (US); Lisa White, Nashville, TN (US); John Phay, Bexley, OH (US); Constantine A. Paras, Nashville, TN (US); Elizabeth Kanter Bartz, Atlanta, GA (US); Matthew D. Keller, Kirkland, WA (US); Nicole Gasparino, St. Petersburg, FL (US); Jennifer Gray Whisenant, Nashville, TN (US); Isaac J. Pence, Crestwood, KY (US)

(73) Assignee: VANDERBILT UNIVERSITY, Nashville, TN (US)

( * ) Notice: Subject to any disclaimer, the term of this patent is extended or adjusted under 35 U.S.C. 154(b) by 1590 days.

(21) Appl. No.: 13/056,469

(22) PCT Filed: Jul. 30, 2009

(86) PCT No.: PCT/US2009/052304
§ 371 (c)(1),
(2), (4) Date: Jun. 14, 2011

(87) PCT Pub. No.: WO2010/014847
PCT Pub. Date: Feb. 4, 2010

(65) Prior Publication Data
US 2012/0010483 A1   Jan. 12, 2012

Related U.S. Application Data

(60) Provisional application No. 61/137,584, filed on Jul. 30, 2008, provisional application No. 61/137,520, filed on Jul. 30, 2008.

(51) Int. Cl.
*A61B 5/1455* (2006.01)
*A61B 5/00* (2006.01)
(Continued)

(52) U.S. Cl.
CPC .......... *A61B 5/415* (2013.01); *A61B 5/0071* (2013.01); *A61B 5/0075* (2013.01);
(Continued)

(58) Field of Classification Search
USPC .............................. 600/310, 317, 476, 478
See application file for complete search history.

(56) References Cited

U.S. PATENT DOCUMENTS 4,930,516 A * 6/1990 Alfano ................. A61B 5/0059
600/477
6,313,146 B1   11/2001 Van Wagenen et al.
(Continued)

FOREIGN PATENT DOCUMENTS

WO   01/50955 A1   7/2001

OTHER PUBLICATIONS

Monici, "Cell and tissue autofluorescence research and diagnostic applications" Biotechnology Annual review, vol. 11 p. 227-256, 2005.*
Liu Gang et al., Raman Spectroscopic Study of Different Human Tissues, Guangpuxue Yu Guangpu Fenxi—Spectroscopy and Spectral Analysis, XP008168107, ISSN: 1000-0593, vol. 25, No. 5, 723-725, Beijing, CN (May 2005).
(Continued)

*Primary Examiner* — Unsu Jung
(74) *Attorney, Agent, or Firm* — Locke Lord LLP; Tim Tingkang Xia, Esq.

(57) ABSTRACT

In one aspect, the present invention relates to a process for intra-operatively providing anatomical guidance in endocrine surgery. In one embodiment, the process includes the steps of illuminating tissues in the neck area of a living subject with a beam of light having a predetermined wavelength, obtaining Raman data from light scattered from the illuminated tissues, finding Raman signatures corresponding to thyroid or parathyroid tissues from the obtained Raman data, and identifying the thyroid or parathyroid tissues from the corresponding Raman signatures.

26 Claims, 17 Drawing Sheets

(51) Int. Cl.
*G01N 21/64* (2006.01)
*G01N 21/65* (2006.01)

(52) U.S. Cl.
CPC ............ *A61B 5/0086* (2013.01); *A61B 5/418* (2013.01); *G01N 21/6456* (2013.01); *G01N 21/65* (2013.01); *A61B 5/4227* (2013.01); *G01N 2021/6439* (2013.01); *G01N 2201/0221* (2013.01)

(56) References Cited

U.S. PATENT DOCUMENTS

| | | | |
|---|---|---|---|
| 6,618,138 | B2 | 9/2003 | Khoury |
| 6,749,565 | B2 | 6/2004 | Chudner |
| 6,831,781 | B2 | 12/2004 | Tearney et al. |
| 7,304,722 | B2 | 12/2007 | Iuliano |
| 2002/0177778 | A1 | 11/2002 | Averback et al. |
| 2005/0245818 | A1 | 11/2005 | Cyrulnik |
| 2008/0154102 | A1* | 6/2008 | Frangioni et al. ............ 600/317 |

OTHER PUBLICATIONS

Michel Manfait et al., Diagnosis and Prognosis of Tissue Pathologies by Raman Microspectroscopy: An Application to Human Thyroid Tumors, Proceedings of SPIE, vol. 3918, 153-160 (May 2000).

European Patent Office (EPO), "Supplementary Partial European Search Report", Mar. 21, 2014, Berlin.

European Patent Office (EPO), "European Search Opinion", Mar. 21, 2014, Berlin.

European Patent Office, "Partial European Search Report for EP Application No. 15187369", Germany, Sep. 12, 2016.

Koppang, Nils, "Canine Ceroid-Lipofuscinosis—A Model for Human Neuronal Ceroid-Liipofuscinosis and Aging", Mechanisms of Ageing and Development, vol. 2, 1973-1974, pp. 421-445.

Prosst, R. L. et al., "Fluorescence-guided minimally invasive parathyroidectomy: a novel detection technique for parathyroid glands", Surgical Endoscopy and Other Interventional techniques, vol. 20, 2006, pp. 1488-1492.

* cited by examiner

1

INTRA-OPERATIVE USE OF FLUORESCENCE SPECTROSCOPY AND APPLICATIONS OF SAME

This application is being filed as PCT International Patent application in the name of Vanderbilt University, a U.S. national corporation, Applicant for all countries except the U.S., and Anita Mahadevan-Jansen, Lisa White, John Phay, Constantine Paras, Elizabeth Kanter, Matt Keller, Nicole Gasparino, and Jennifer Whisenant, all U.S. residents, Applicants for the designation of the U.S. only, on 30 Jul. 2009.

CROSS-REFERENCE TO RELATED PATENT APPLICATION

This application claims priority to and the benefit of, pursuant to 35 U.S.C. §119(e), U.S. provisional patent application Ser. No. 61/137,520, filed Jul. 30, 2008, entitled "Intraoperative Use of Fluorescence Spectroscopy," by Constantine Paras, Anita Mahadevan-Jansen, Matt Keller, John Phay and Lisa White, the contents of which is incorporated herein in its entirety by reference.

This application also claims priority to and the benefit of, pursuant to 35 U.S.C. §119(e), U.S. provisional patent application Ser. No. 61/137,584, filed Jul. 30, 2008, entitled "Intraoperative Parathyroid Detector and Applications of Same," by Lisa White, John Phay, Anita Mahadevan-Jansen, Elizabeth Kanter, Matt Keller, Nicole Gasparino and Jennifer Whisenant, the contents of which is incorporated herein in its entirety by reference.

Some references, if any, which may include patents, patent applications and various publications, are cited in a reference list and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [6] represents the 6th reference cited in the reference list, namely, Frilling, A. & Weber, F. Complications in Thyroid and Parathyroid Surgery in *Surgery of the Thyroid and Parathyroid Glands* 217-224 (2007).

FIELD OF THE INVENTION

The present invention relates generally to near-infrared optical detection, and more particularly to intra-operative near-infrared optical detection and applications of the same.

BACKGROUND OF THE INVENTION

The endocrine system is a complex system of organs and glands which includes the thyroid and parathyroid. The anatomy of the neck is illustrated in FIG. 1. The thyroid gland regulates many developmental and metabolic processes. Common diseases of the thyroid include goiters, hyperthyroidism, hypothyroidism, benign and malignant nodules, and autoimmune diseases such as Graves' disease. Surgery is the most common treatment for Graves's disease, goiters, benign thyroid nodules, and thyroid cancers.

The parathyroid normally lies within the same region as the thyroid in the neck and functions to control calcium levels in the blood. The most common parathyroid disorder is primary hyperparathyroidism, in which one or more of the parathyroid glands become enlarged and hyperactive. This causes excess secretion of parathyroid hormone and a disruption in normal bone and mineral metabolism. The prevalence of primary hyperparathyroidism has been estimated at 21 cases per 100,000 person-years. In 80% of cases, primary hyperparathyroidism is caused by a single overactive parathyroid gland and surgical removal of the diseased parathyroid gland is the only definitive treatment.

Typically there are four tan parathyroid glands, each approximately 6 to 8 mm in size. They are typically positioned within the neck but can vary in location within the body and are sometimes intrathymic. Due to their small size and variability in position, the parathyroid glands are often difficult to distinguish from surrounding tissue and thyroid in the neck. The parathyroid visually resembles its surrounding tissue and this can extend surgical time during a parathyroidectomy, during which the surgeon is simply searching for the small organ. Accidental removal or damage to healthy parathyroids during parathyroid or thyroid surgery can result in serious complications such as hypocalcemia or hypoparathyroidism. Hypoparathyroidism may result from direct injury, devascularization, and/or disruption of the parathyroid glands. Statistics suggest that temporary and permanent hypoparathyroidism rates are between 4-20% during thyroid surgery. The most common complications of both parathyroid and thyroid surgery are postoperative hypocalcemia, vocal-cord paralysis, and hematoma.

The current surgical procedure for thyroid and parathyroid surgeries involves a systematic search within the neck in which the surgeon is mainly relying on visual inspection to identify target tissues. The incidence of complications occurring due to this subjective method is directly proportional to the extent of thyroidectomy and inversely proportional to the experience of the surgeon. The disadvantages to the current method include the lengthy duration of the surgery, the exploratory nature of the surgery, and the lack of sensitive and applicable preoperative and intra-operative imaging. Confirmation of removal of the diseased parathyroid relies on histopathology or post-operative diagnosis of symptoms. There is a need for reliable methods for identifying the parathyroid glands intraoperatively. Moreover, while surgical guidance systems have been developed and utilized for brain surgery and other organ surgery procedures, none is available for thyroid and parathyroid surgeries.

Therefore, a heretofore unaddressed need exists in the art to address the aforementioned deficiencies and inadequacies.

SUMMARY OF THE INVENTION

In one aspect, the present invention relates to a process for intra-operatively providing anatomical guidance in endocrine surgery. In one embodiment, the process includes the steps of illuminating tissues in the neck area of a living subject with a beam of light having a predetermined wavelength, obtaining Raman data from light scattered from the illuminated tissues, finding Raman signatures corresponding to thyroid or parathyroid tissues from the obtained Raman data, and identifying the thyroid or parathyroid tissues from the corresponding Raman signatures.

In one embodiment, the step of obtaining the Raman data includes collecting the scattered light with a collection probe and obtaining a corresponding Raman spectrum with a Raman spectrometer. In this embodiment, the predetermined wavelength is in the near-infrared range and the obtained Raman data includes near-infrared Raman data. Further, the step of finding Raman signatures from the obtained Raman data includes processing the obtained Raman spectrum.

In another aspect, the present invention relates to a system for intra-operatively providing anatomical guidance in endocrine surgery. In one embodiment, the system includes a light source configured to emit light having a predetermined wavelength, an optical probe optically connected to the light source and configured to deliver a beam of light to tissues in the neck area of a living subject and to collect light scattered from the tissues, a detector optically coupled with the optical probe, for obtaining Raman data from the collected scattered light and rejecting signals from within the optical probe, and a controller in communication with the detector and programmed for finding Raman signatures corresponding to thyroid or parathyroid tissues from the obtained Raman data and identifying tissues that correspond to the Raman signatures as thyroid or parathyroid tissues.

In one embodiment, the predetermined wavelength is in the near-infrared range. The optical probe includes a collection probe and the detector includes a spectrometer. The system further includes an optical fiber means that is optically coupled to the light source, for receiving the beam of light from the light source and delivering the beam of light to the tissues.

In yet another aspect, the present invention relates to a process for intra-operatively identifying parathyroid tissues of a living subject. In one embodiment, the process includes the steps of illuminating tissues in the neck area of the living subject with a beam of light having a predetermined wavelength, obtaining an auto-fluorescence spectrum of intensity from the light emitted from the illuminated tissues, finding the highest peak intensity in the auto-fluorescence spectrum, and identifying tissues that correspond to the highest peak intensity.

In one embodiment, the predetermined wavelength is in the near-infrared range. The step of obtaining the auto-fluorescence spectrum of intensity includes collecting the light emitted from the illuminated tissues with a collection probe and obtaining the fluorescence spectrum with a fluorescence spectrometer. The step of identifying tissues comprises identifying tissues corresponding to the highest peak in the auto-fluorescence spectrum as parathyroid tissues. The process further includes the steps of finding the second highest peak intensity in the auto-fluorescence spectrum and identifying tissues corresponding to the second highest peak intensity as thyroid tissues. Moreover, the process further includes the step of displaying images visually representing the auto-fluorescence spectrum in real time to a medical professional performing the endocrine surgery.

In yet another aspect, the present invention relates to a system for intra-operatively identifying parathyroid tissues of a living subject. In one embodiment, the system includes means for illuminating tissues in a target region in the neck area of the living subject, means for collecting light emitted from the tissues in response to the illumination, means for obtaining a auto-fluorescence spectrum of intensity from the collected light, means for finding a highest peak in the auto-fluorescence spectrum, and means for identifying tissues corresponding to the highest peak as parathyroid tissues.

In one embodiment, the means for illuminating the tissues is a light source configured to emit a beam of light having a wavelength in the near-infrared range. The system further includes an optical fiber means optically coupled to the light source, for receiving the beam of light from the light source and delivering the received beam of light to the tissues. In this embodiment, the means for obtaining the auto-fluorescence spectrum of intensity includes a collection probe and a fluorescence spectrometer. The system also includes means for displaying real-time images visually representing the auto-fluorescence spectrum to a medical professional performing an endocrine surgical procedure.

In yet another embodiment, the present invention relates to a process for intra-operatively providing anatomical guidance in endocrine surgery. In one embodiment, the process includes the steps of illuminating tissues in the neck area of a living subject with a beam of light having a predetermined wavelength, obtaining auto-fluorescence data from light emitted from the tissues in response to the illumination, and displaying images of the obtained auto-fluorescence data on a display for providing anatomical guidance to a medical professional performing the endocrine surgery.

In one embodiment, the predetermined wavelength is in the near-infrared range, and the auto-fluorescence data includes near-infrared auto-fluorescence data. The auto-fluorescence data includes a auto-fluorescence spectrum with a highest peak intensity and a second highest peak intensity. The tissues that produce the highest peak in the auto-fluorescence spectrum correspond to parathyroid tissues and the tissues that produce the second highest peak in the auto-fluorescence spectrum correspond to thyroid tissues.

In yet another aspect, the present invention relates to a system for intra-operatively providing anatomical guidance in endocrine surgery. In one embodiment, the system includes a light source for illuminating tissues in the neck area of a living subject with a beam of light, means for obtaining auto-fluorescence data from light emitted from the illuminated tissues, and a display in communication with the means for obtaining auto-fluorescence data and configured to display images generated from the obtained auto-fluorescence data, for providing anatomical guidance in an endocrine surgery. The light source includes a laser configured to emit light having a wavelength in the near-infrared range.

In yet another aspect, the present invention relates to a process for intra-operatively providing disease detection in endocrine surgery. In one embodiment, the process includes the steps of illuminating tissues in the neck area of a living subject, obtaining Raman data from light scattered from the illuminated tissues, finding Raman signatures corresponding to diseased thyroid or parathyroid tissues from the obtained Raman data, and identifying the diseased thyroid or parathyroid tissues from the corresponding Raman signatures.

In one embodiment, the illuminating step includes illuminating the tissues with a beam of light from a near-infrared light source. The step of obtaining the Raman data includes collecting the scattered light in a collection probe and obtaining Raman spectra from the Raman data with a Raman spectrometer. The step of finding Raman signatures from the obtained Raman data includes processing the obtained Raman spectra.

In yet another aspect, the present invention relates to a system for intra-operatively providing disease detection in endocrine surgery. In one embodiment, the system includes a light source, an optical probe optically connected to the light source and configured to deliver a beam of light to tissues in the neck area of a living subject and collect light scattered from the tissues, a detector optically coupled with the optical probe, for obtaining Raman data from the collected light while rejecting signals generated from within the probe itself, and a computer in communication with the detector and programmed for finding Raman signatures from the obtained Raman data and identifying tissues corresponding to the Raman signatures as representing thyroid or parathyroid disease.

In one embodiment, the light source includes a near-infrared laser. In this embodiment, the system further includes an optical fiber means optically coupled to the light source, for receiving the beam of light from the light source and delivering the received beam of light to the tissues, and the detector comprises a spectrometer.

In one embodiment, the illuminating step includes illuminating the tissues with a beam of light from a near-infrared light source. The step of obtaining the auto-fluorescence spectrum includes collecting the emitted light in a collection probe and obtaining the auto-fluorescence spectrum with a fluorescence spectrometer. The step of finding the peak intensity in the auto-fluorescence spectrum includes displaying the auto-fluorescence spectrum and comparing the auto-fluorescence spectrum to a baseline spectrum for non-fluorescent tissues. The process further includes the step of displaying images visually representing the auto-fluorescence spectrum in a display for guiding a medical professional through an endocrine surgery.

In yet another aspect, the present invention relates to a system for intra-operatively identifying thyroid or parathyroid cells of a living subject. In one embodiment, the system includes a light source for illuminating tissues in the neck area of the living subject, an optical probe for collecting light emitted from the illuminated tissues, means for obtaining a auto-fluorescence spectrum of intensity from the collected light, means for finding a peak intensity in the auto-fluorescence spectrum, means for comparing the auto-fluorescence spectrum to a baseline spectrum, means for identifying the presence of parathyroid or thyroid cells from the peak intensity in the auto-fluorescence spectrum.

In one embodiment, the light source includes a near-infrared laser. The system further includes optical fiber means optically coupled to the light source, for receiving a beam of light from the light source and delivering the received beam of light to the tissues in the neck area of the living subject. The means for obtaining the auto-fluorescence spectrum includes a fluorescence spectrometer. In this embodiment, the system also includes a controller in communication with the fluorescence spectrometer and programmed for comparing a baseline auto-fluorescence spectrum of non-fluorescent tissues to the obtained auto-fluorescence spectrum, identifying the presence of thyroid or parathyroid cells from the comparison, and displaying the images visually representing the auto-fluorescence spectrum for guiding a medical professional through an endocrine surgery.

In yet a further aspect, the present invention relates to a system for intraoperatively detecting the presence of infiltrating cells in the lymph nodes and surrounding tissues. In one embodiment, the process includes the steps of illuminating human tissues in the neck area of a human being in operation with a beam of light; obtaining auto-fluorescence data from the light emitted from the human tissues; and detecting higher levels of auto-fluorescence in typically non fluorescing tissues.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment, and wherein.

DETAILED DESCRIPTION OF THE INVENTION

Figure 1:
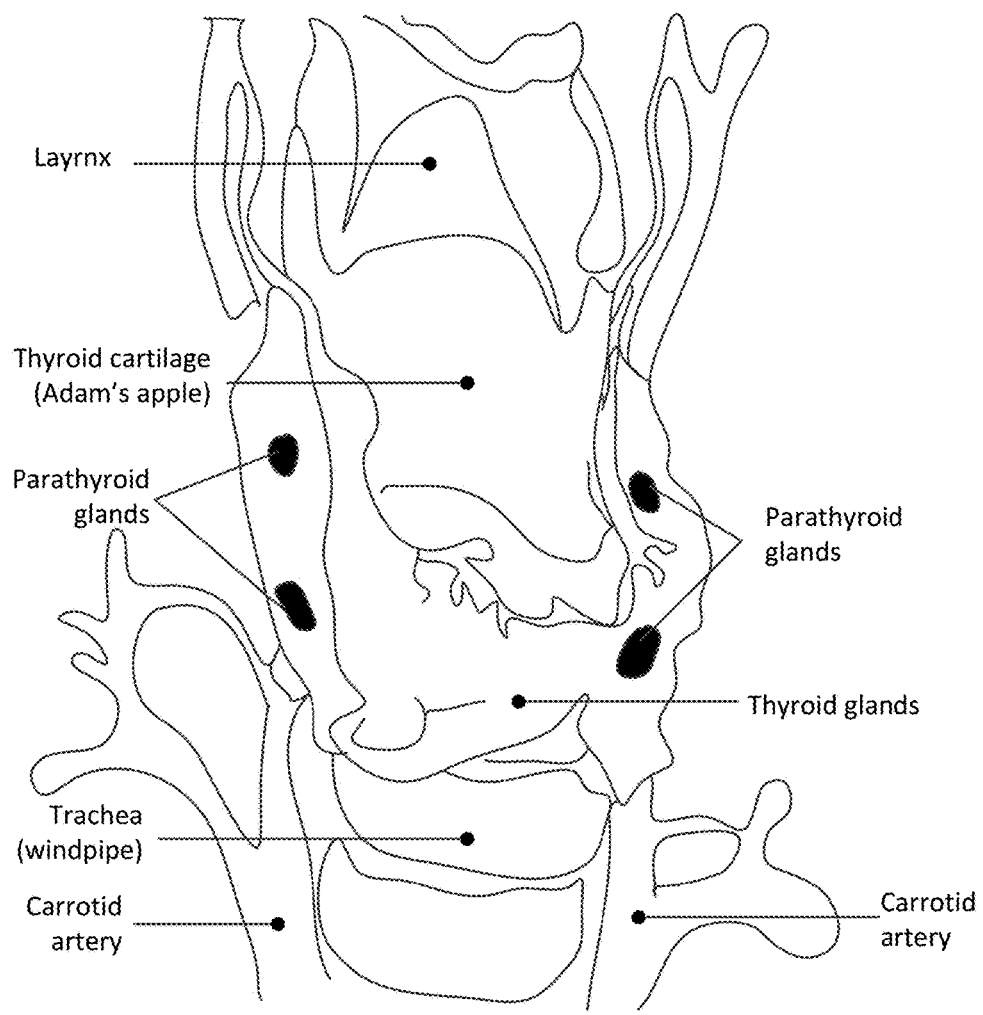
FIG. 1 shows a general view of the anatomy of human thyroid/parathyroid glands.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "living subject" refers to a human being such as a patient, or an animal such as a lab testing monkey.

As used herein, the term "Raman spectroscopy" refers to an optical technique that probes the specific molecular content of a sample by collecting inelastically scattered light. As photons propagate through a medium, they undergo both absorptive and scattering events. In absorption, the energy of the photons is completely transferred to the material, allowing either heat transfer (internal conversion) or re-emission phenomena such as fluorescence and phosphorescence to occur. Scattering, however, is normally an elastic process, in which the incident photons retain their energy. In Raman scattering, the photons either donate or acquire energy from the medium, on a molecular level making it an inelastic process. In contrast to fluorescence, where the energy transfers are on the order of the electronic bandgaps, the energy transfers associated with Raman scattering are on the order of the vibrational modes of the molecule. These vibrational modes are molecularly specific, giving every molecule a unique Raman spectral signature.

Raman scattering is a very weak phenomena, and therefore practical measurement of Raman spectra of a medium requires high power excitation laser sources and extremely sensitive detection hardware. Even with these components, the Raman spectra from tissue are masked by the relatively intense tissue auto-fluorescence. After detection, post processing techniques are required to subtract the fluorescence background and enable accurate visualization of the Raman spectra. Raman spectra are plotted as a function of frequency shift in units of wavenumber ($cm^{-1}$). The region of the Raman spectra where most biological molecules have Raman peaks is from 500 to 2000 $cm^{-1}$. In contrast to fluorescence spectra, Raman spectra have sharp spectral features that enable easier identification of the constituent sources of spectral peaks in a complex sample. In the context of detecting the changes that cancerous tissues undergo, differences in the Raman spectral features that correlate to the increased nucleic acid content in neoplastic cells has been observed.

The term "fluorescence spectroscopy" or its synonyms "fluorometry" or "spectrofluorometry" refers to a type of electromagnetic spectroscopy which analyzes fluorescence from a sample. It involves using a beam of light, usually ultraviolet light, that excites the electrons in molecules of certain compounds and causes them to emit light of a lower energy, typically, but not necessarily, visible light. A complementary technique is absorption spectroscopy.

Fluorescence spectroscopy utilizes that fact that molecules have various states referred to as energy levels. Fluorescence spectroscopy is primarily concerned with electronic and vibrational states of energy. Generally, the sample being examined will have a ground electronic state (a low energy state) of interest, and an excited electronic state of higher energy. Within each of these electronic states are various vibrational states.

In fluorescence spectroscopy, the sample is first excited, by absorbing a photon, from its ground electronic state to one of the various vibrational states in the excited electronic state. Collisions with other molecules cause the excited molecule to lose vibrational energy until it reaches the lowest vibrational state of the excited electronic state.

The molecule then drops down to one of the various vibrational levels of the ground electronic state again, emitting a photon in the process. As molecules may drop down into any of several vibrational levels in the ground state, the emitted photons will have different energies, and thus frequencies. Therefore, by analyzing the different frequencies of light emitted in fluorescence spectroscopy, along with their relative intensities, the structure of the different vibrational levels can be determined.

In a typical measurement, the different frequencies of fluorescence light emitted by a sample are measured, holding the excitation light at a constant wavelength. This is called an emission spectrum. An excitation spectrum is measured by recording a number of emission spectra using different wavelengths of excitation light.

As used in herein, the term "auto-fluorescence" refers to the fluorescence produced by a molecule of interest without the use of exogenous markers. Auto-fluorescence may serve as a useful diagnostic indicator such as in the case of "biological auto-fluorescence", which refers to the fact that cells contain molecules, which become fluorescent when excited by UV/VIS (typically 400-700 nm) radiation of suitable wavelength. This fluorescence emission, arising from endogenous fluorophores, is an intrinsic property of cells and is called auto-fluorescence to be distinguished from fluorescence signals obtained by adding exogenous markers. The majority of cell auto-fluorescence originates from mitochondria and lysosomes. Together with aromatic amino acids and lipo-pigments, the most important endogenous fluorophores are pyridinic (NADPH) and flavin coenzymes. In tissues, the extracellular matrix often contributes to the auto-fluorescence emission more than the cellular component, because collagen and elastin have, among the endogenous fluorophores, a relatively high quantum yield. Changes occurring in the cell and tissue state during physiological and/or pathological processes result in modifications of the amount and distribution of endogenous fluorophores and chemical-physical properties of their microenvironment. Therefore, analytical techniques based on auto-fluorescence monitoring may be utilized in order to obtain information about morphological and physiological state of cells and tissues. Moreover, auto-fluorescence analysis can be performed in real time because it does not require any treatment of fixing or staining of the specimens. In the past few years spectroscopic and imaging techniques have been developed for many different applications both in basic research and diagnostics [13]. The present invention provides a case where auto-fluorescence finds good use.

As used herein, "charge-coupled device" or "CCD" refers to an analog shift register that enables the transportation of analog signals (electric charges) through successive stages (capacitors), controlled by a clock signal. Charge-coupled devices can be used as a form of memory or for delaying samples of analog signals. Today, they are most widely used in arrays of photoelectric light sensors to serialize parallel analog signals. In a CCD for capturing images, there is a photoactive region (an epitaxial layer of silicon), and a transmission region made out of a shift register (the CCD, properly speaking).

An image is projected through a lens onto the capacitor array (the photoactive region), causing each capacitor to accumulate an electric charge proportional to the light intensity at that location. A one-dimensional array, used in line-scan cameras, captures a single slice of the image, while a two-dimensional array, used in video and still cameras, captures a two-dimensional picture corresponding to the scene projected onto the focal plane of the sensor. Once the array has been exposed to the image, a control circuit causes each capacitor to transfer its contents to its neighbor (operating as a shift register). The last capacitor in the array dumps its charge into a charge amplifier, which converts the charge into a voltage. By repeating this process, the controlling circuit converts the entire semiconductor contents of the array to a sequence of voltages, which it samples, digitizes and stores in some form of memory.

As used herein, "plurality" means two or more.

As used herein, the terms "comprising," "including," "carrying," "having," "containing," "involving," and the like are to be understood to be open-ended, i.e., to mean including but not limited to.

OVERVIEW OF THE INVENTION

As set forth above, thyroid and parathyroid diseases combine the fields of endocrinology and oncology leading to a complex combination of conditions [1]. When the disease cannot be treated by other methods, surgical means are used to remove the diseased gland(s). The thyroid gland, parathyroid glands, nerves, adipose tissue, and lymph nodes are closely positioned in the neck region. Due to their close proximity and tendency to blend into each other, many of these structures, specifically the parathyroid glands, are difficult to distinguish visually during endocrine surgery. The situation is further complicated by its small size and variability in position. Surgeons must ultimately rely on visual inspection to identify the different tissues, which can be subjective and often inconclusive [2, 3]. Complications occur when the parathyroid is accidentally injured or removed during thyroidectomies or only partially removed in the case of parathyroidectomies [4].

Existing methods for identifying parathyroid glands are limited and have deficiencies that can result in surgical complications [5]. Current technology relies on histopathology or post-operative diagnosis of symptoms to determine if the parathyroid was accidentally or incompletely removed [6]. An accurate, automated diagnostic method could allow faster, more effective patient management [7, 8]. Optical spectroscopy can detect differences in tissue architecture and biochemical composition. In particular, fluorescence spectroscopy has been of considerable interest in the development of new clinical diagnostic tools. Fluorescence measurements of human tissue can be made in real-time, without tissue removal and diagnosis based on tissue fluorescence can be easily automated [9]. Fluorescence molecules typically exhibit signal in the UV/VIS wavelengths, or about 400-700 nm [10]. As excitation wavelengths become longer, auto-fluorescence decreases [10]. It is believed that for the first time, near-infrared auto-fluorescence has been utilized in the present invention and attractive to the inventors due to their increased penetration depth in biological tissues. In one aspect, the present invention provides, among other things, a process or method of using near-infrared auto-fluorescence for the identification of the parathyroid in vivo during endocrine surgery. Such a method could prevent accidental or incomplete removal of parathyroid glands.

In another aspect, the present invention provides real time imaging systems that can detect the near-infrared auto-fluorescence from the tissues in the neck in real time to guide surgical resection or surgical procedure.

In one embodiment, an imaging system was built to detect near-infrared auto-fluorescence. The system includes a near-infrared light source for emitting a beam of near-infrared light, a light guide or optical fiber(s) that delivers the light to the tissue, a camera with a filter to block unwanted wavelenghts, and a computer with a controller in communication with each component/device of the system to coordinate the image capture. In operation, tissue was placed under the camera, the near-infrared auto-fluorescence from the tissue was collected and acquired through the camera, and stored in a memory for further processing.

In another embodiment, an imaging system provides an x-y image (or video image) of the field including NIR wavelengths with the sensitivity needed for tissue auto-fluorescence measurements. An exemplary device was built with a FIND-R-SCOPE®. Such a system can be made as a portable, hand-held device, in which the image is viewed through a built-in viewer by a user such as a surgeon to see the auto-fluorescence from the tissue or from the targeted area of the tissues on site. The viewer can also be connected to a display with or without a camera attachment. The imaging system can be used to guide the surgeon intraoperatively through a surgical procedure to identify the tissues that need to be acted on.

In short, according to several embodiments of the present invention, near-infrared (NIR) auto-fluorescence is used to identify parathyroid glands during thyroid and parathyroidectomies. The present invention utilized the discovery that parathyroid tissue had unique optical signals to identify the parathyroid glands and differentiate them from other tissues in the neck intra-operatively, in which the intensity of the parathyroid signal was compared to the auto-fluorescence of the surrounding tissue including the thyroid gland. Several fluorescence measurements were conducted according to the present invention on patients who were undergone endocrine surgery at the Vanderbilt University Medical Center. In each of the measurements, the parathyroid had markedly higher levels of auto-fluorescence. These results indicate that NIR auto-fluorescence provides an excellent tool to locate parathyroid tissue in endocrine surgery.

Further description will be made as to the embodiments of the present invention in conjunction with the accompanying drawings of FIGS. 1-9.

IMPLEMENTATIONS AND EXAMPLES OF THE INVENTION

Without intent to limit the scope of the invention, exemplary methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

This example in part illustrates a method or process, with corresponding apparatus or system, according to one embodiment of the present invention.

Figure 3A:
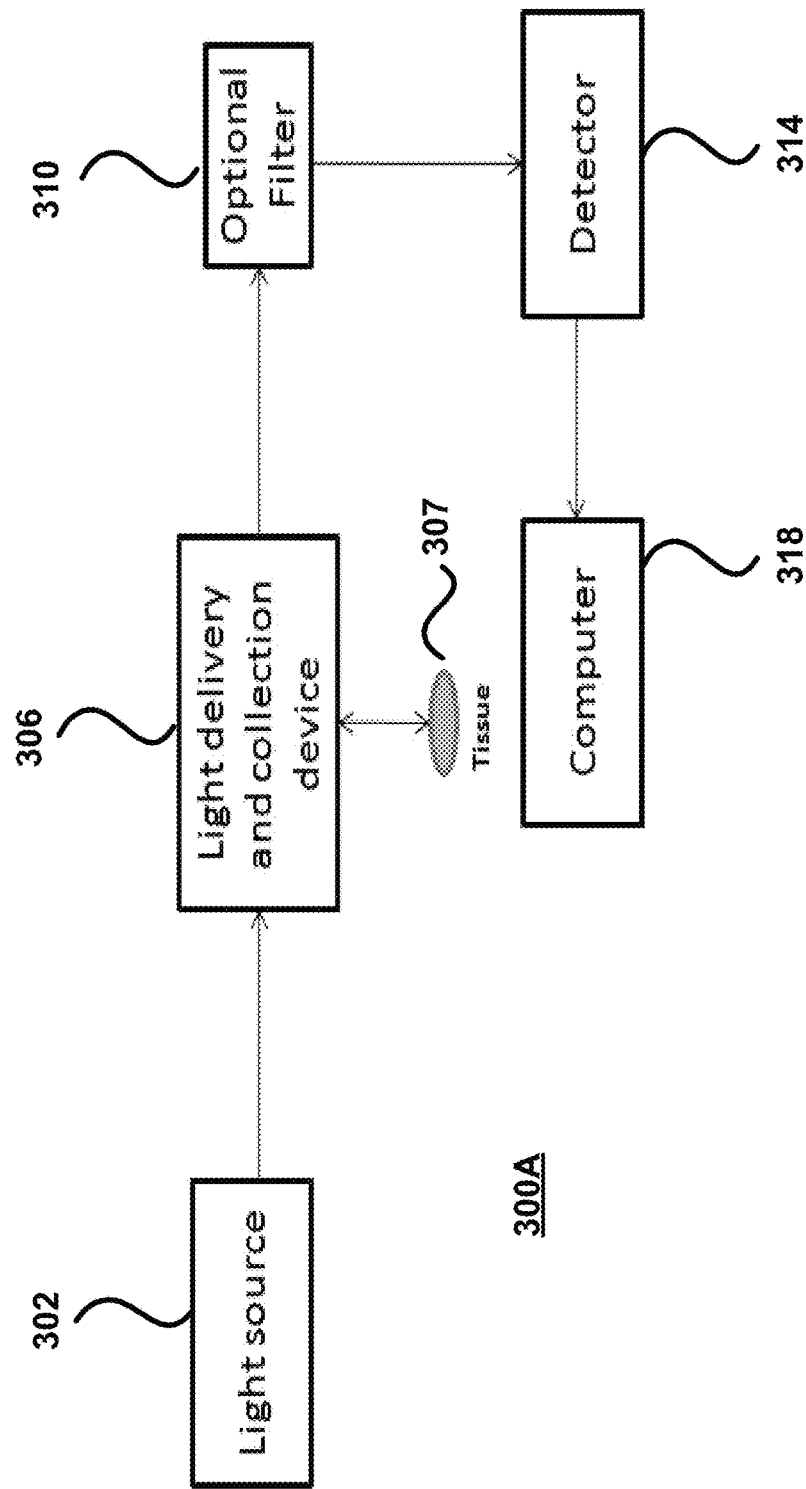
FIG. 3A schematically shows a system according to another embodiment of the present invention.
Figure 3B:
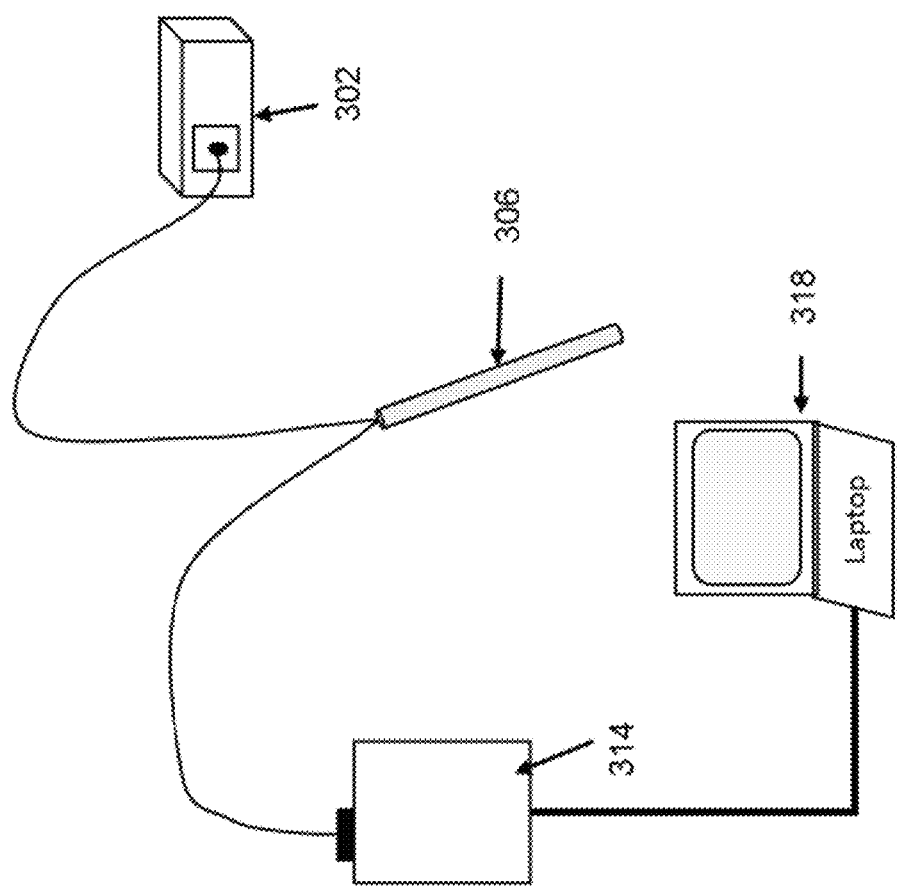
FIG. 3B is a photo of a system reduced to practice, which is corresponding to a system according to the embodiment of the present invention as shown in FIG. 4A.
Figure 3C:
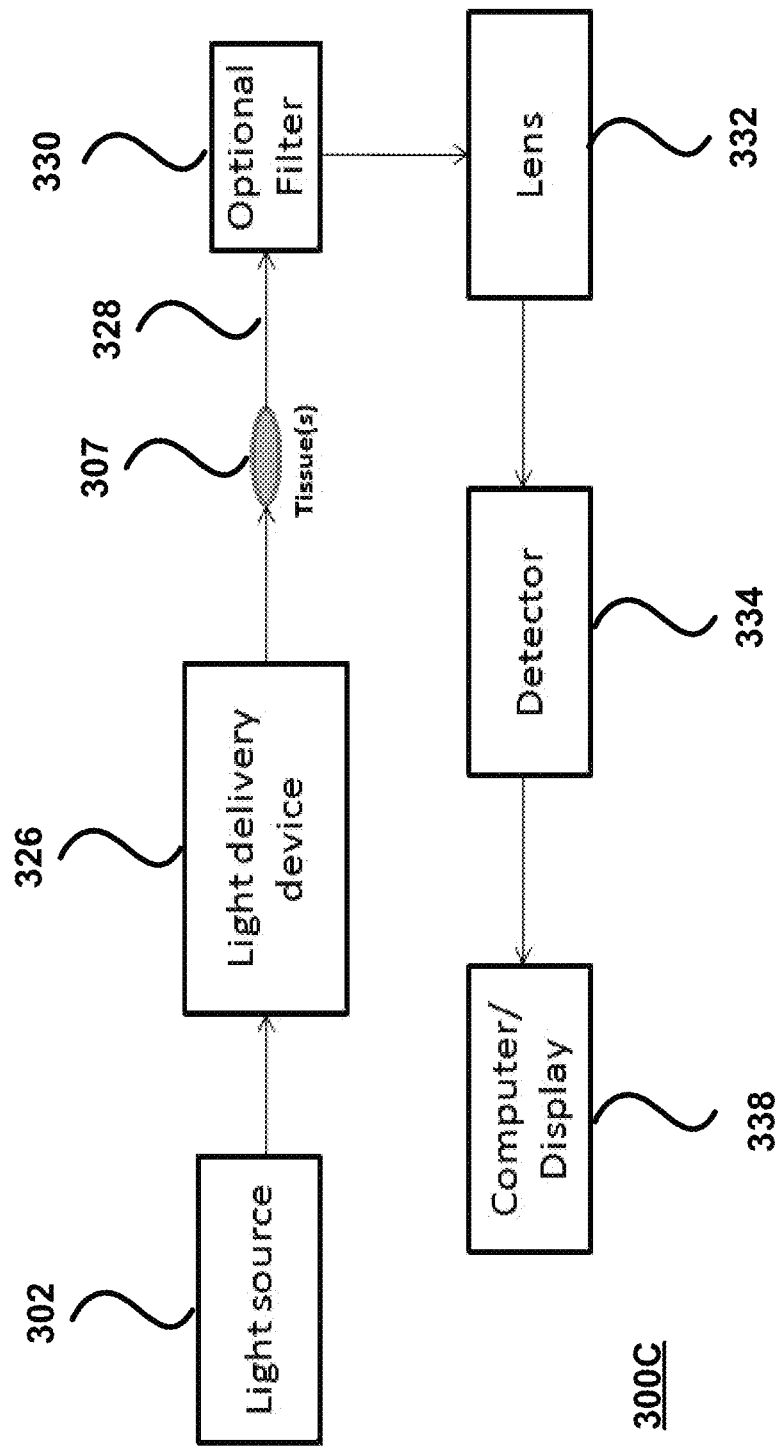
FIG. 3C schematically shows a system according to yet another embodiment of the present invention.
Figure 3D:
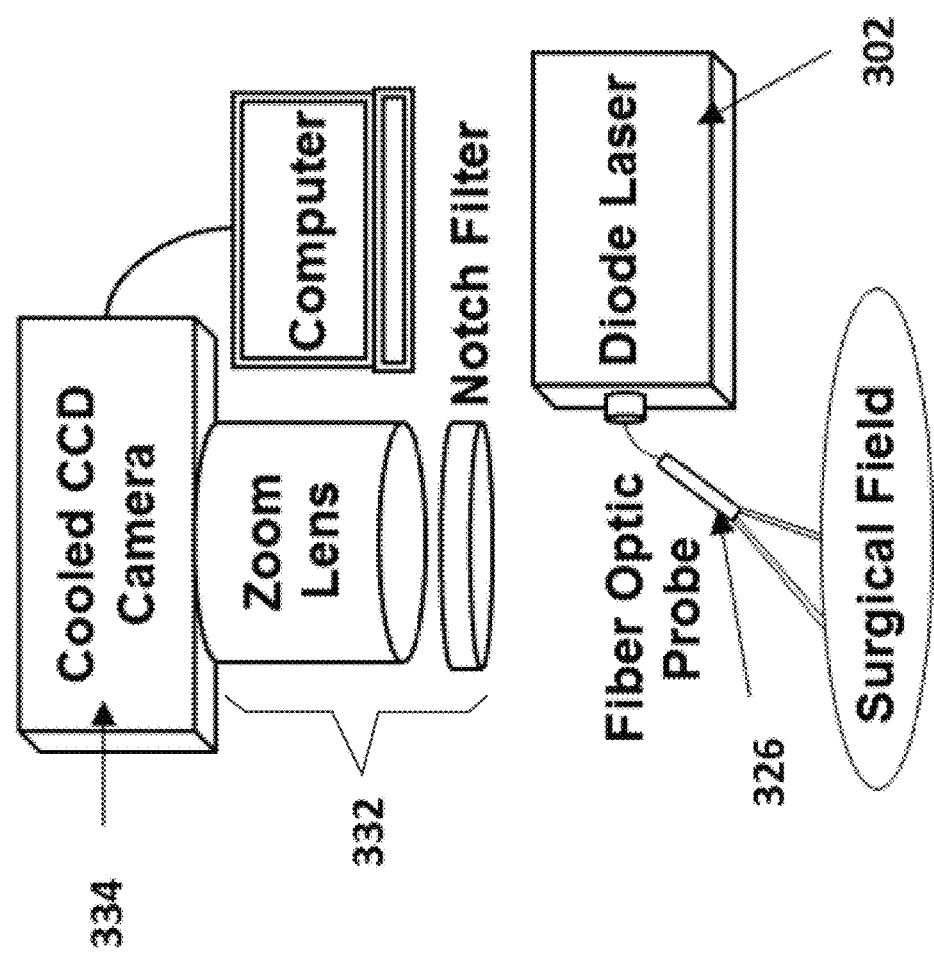
FIG. 3D is a photo of a system reduced to practice, which is corresponding to the embodiment of the present invention as shown in FIG. 4C.
Figure 3E:
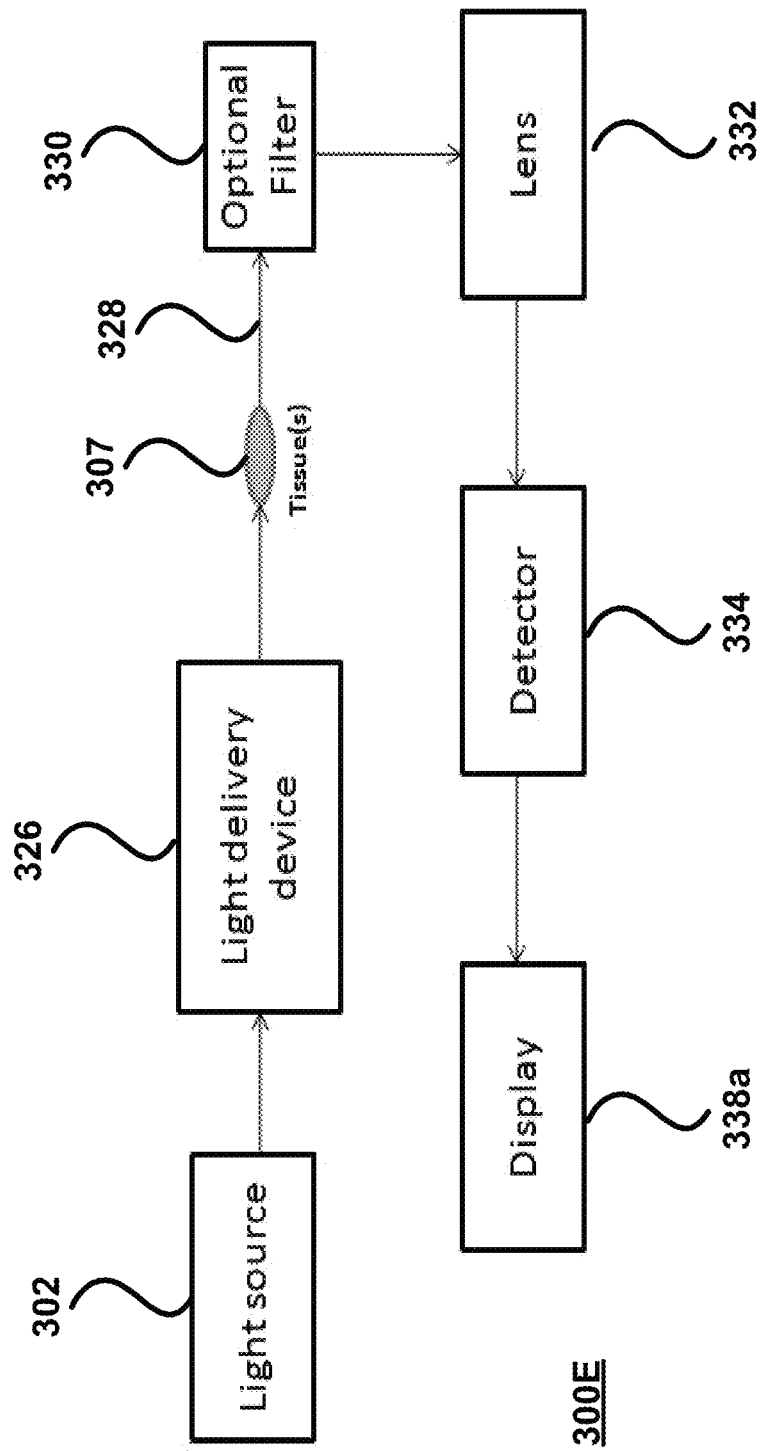
FIG. 3E schematically shows a system according to a further embodiment of the present invention.

Referring now to FIG. 3E, a system 300E is schematically shown in a block diagram. The system 300E has a light source 302, which is designed to provide a beam of light with appropriate excitation wavelengths and energy so as to excite certain molecules of sample tissue 307, when receiving the beam of light, to generate auto-fluorescence emission. The system 300E also has a light delivery device 326, which is optically coupled with the light source 302 and delivers the beam of light from the light source 302 to the tissue 307. An optional filter 330 can be strategically positioned in an optical path 328 along which optical signals emitted from the tissue 307 responsive to the incident beam of light travel and utilized to reduce excess wavelengths and/or ambient light to ensure desirable optical signals to be detected. The system 300E further has a detector 334, which detects and records the optical signals emitted from the tissue 307. A lens 332 is positioned between the tissue 307 and the detector 334 to receive the optical signals emitted from the tissue and focus them on a desired spot on the detector 334. If an optional filter 330 is utilized, lens 332 will be positioned between the optional filter 330 and the detector 334. A display 338a, which has imaging processing and display capacity, is at least in communication with the detector 334, where the display 338a is adapted with appropriate controller cards and software to control signal acquisition, process data and display spectra, among other things. The display 338a displays instant images corresponding to the optical signals emitted from the tissue 307, which may guide a surgeon or a medical professional through a medical procedure to identify tissues and act on them accordingly.

Figure 3F:
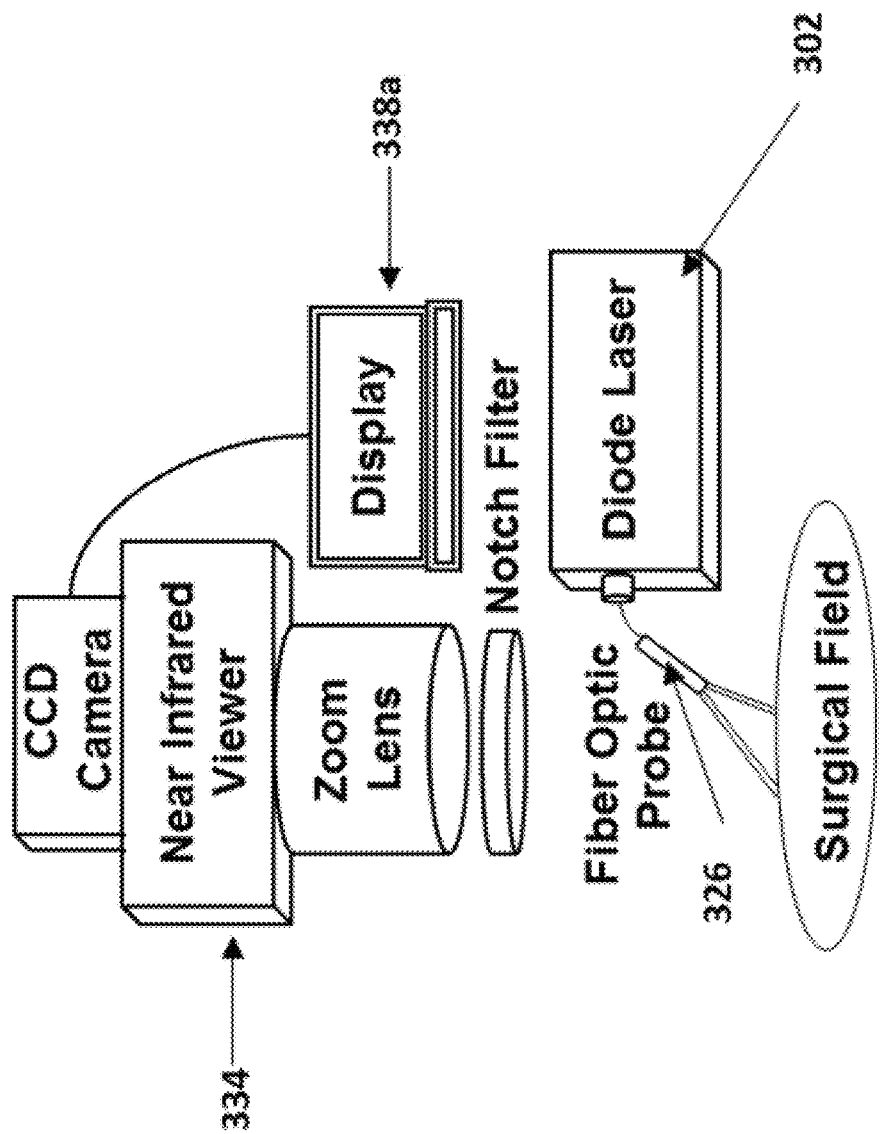
FIG. 3F is a photo of a system reduced to practice, which is corresponding to a system according to the embodiment of the present invention as shown in FIG. 3E.

FIG. 3F shows a photo of a system corresponding to system 300E of FIG. 3E, which was reduced to practice.

A system according to one embodiment of the present invention allows a surgeon to correctly differentiate between thyroid and parathyroid tissue intra-operatively and immediately. Due to their differing optical properties, thyroid, parathyroid and the surrounding neck tissues can be easily differentiated intra-operatively by the system. When a 785 nm laser excites a neck area of tissue, the parathyroid fluoresces with a greater intensity than the surrounding thyroid tissue. Normal tissues other than thyroid or parathyroid in the neck region will not create detectable auto-fluorescence. Both the thyroid and parathyroid fluoresce at about 822 nm, with the parathyroid fluorescing with greater intensity. The system described in this Example allows the 822 nm light created by the thyroid and parathyroid to be viewed directly by the surgeon as visible light. The parathyroid visualization unit according to one embodiment of the present invention is easy to use, requiring as little training as possible. It also effectively decreases operative time and the number of unsuccessful operations, thereby greatly reducing the need for costly secondary operations. More importantly, the system would reduce the rate of accidental removal or injury to the parathyroid. The system may be coupled with equipment already present in the operating room ("OR").

There are currently no methods consistently used intra-operatively to differentiate between thyroid and parathyroid tissue. The system according to one embodiment of the present invention has following features: it uses optical fibers running from a light source such as a 785 nm laser source to excite the tissue. The system has a display device, allowing for the surgeon to view the differing auto-fluorescence of the two or more tissue types, instead of interpreting a numerical intensity value. The system is attachable to a head-unit that the surgeon could wear during surgery.

The new system is in real-time. This real-time factor could decrease time in the OR by creating an intra-operative imaging modality. This would eliminate the need to send tissue samples to histology simply to determine tissue type during surgery and thus reduce any wait times associated with this. The system is adapted to be able to excite an area equal to the size of the surgeon's incision.

Methodology.

To allow the system, according to one embodiment of the present invention, to have visualization ability, several cameras and viewers were tried and/or evaluated to determine which would be most suitable for this feature. A viewer system with peak sensitivity around 825 nm and the ability to visually show the surgeon the NIR light within the visual spectrum was needed. The FIND-R-SCOPE® Infrared Viewer Model 84499A was the final choice. This viewer has spectral sensitivity from 350 to 1350 nm with peak sensitivity at 800 nm, very close to the 822 nm fluorescence coming from the parathyroid tissue. This model is also lightweight, a feature preferred for attachment to a head-unit. To view only the auto-fluorescence of the tissue, an 820 nm long pass filter was placed in front of the viewer. This was important because it removed the high intensity 785 nm laser light as well as visible light and would reduce any background signal from overhead lights during surgery.

Additionally, the different means of exciting a larger area of tissue than a laser independently would excite was tried and/or evaluated. The diameter of the laser beam was measured at approximately 0.3 cm which is rather smaller than the desired one square centimeter. A liquid light guide was utilized because it would excite the desired area of tissue while, at the same time, maintaining the power necessary to excite the tissue. A liquid light guide from Newport® (Model: 77639 Liquid Light Guide, 420-2000 nm, 0.3 in Core, 3.9 in Bend Radius, 79 in Length) was used in practice. This liquid light guide is compatible with light in the NIR, has a great enough numerical aperture such that a fiber from the laser could be directly coupled into the liquid light guide, and is long enough to allow the laser source to be separate from the excitation-detection system. Other liquid light guides having comparable parameters can also be utilized to practice the present invention.

Figure 2:
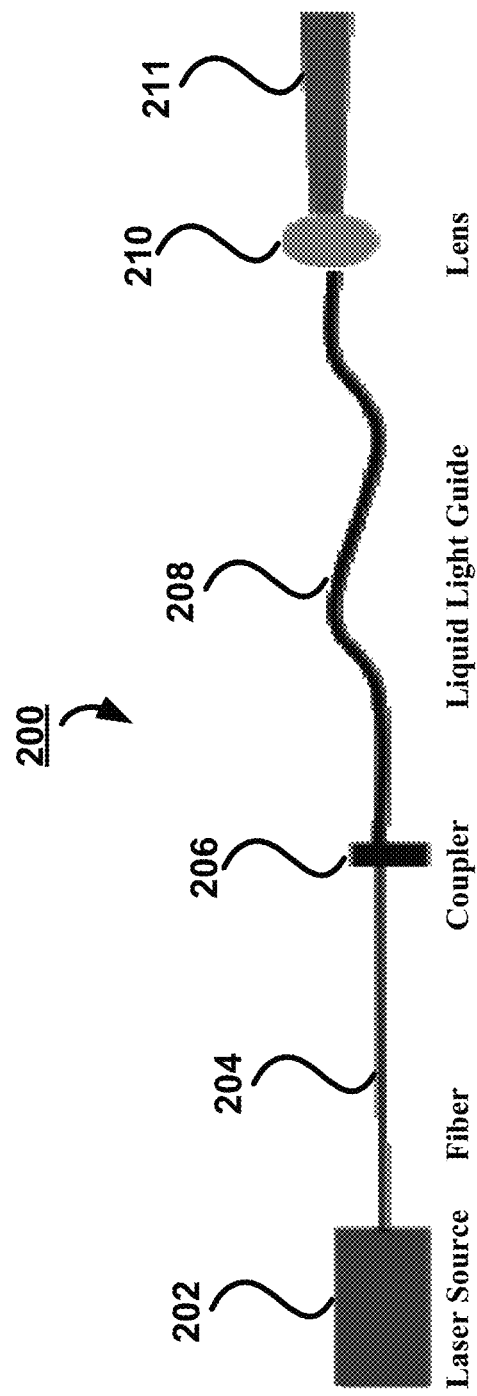
FIG. 2 schematically shows an excitation system that is utilized in one embodiment of the present invention.

The excitation setup of the system according to one embodiment of the present invention, as shown in FIG. 2, used a 785 nm laser 202 coupled to an optical fiber 204 with a diameter of 400 µm and a numerical aperture of 0.22. This cable 204 was then directly coupled to the liquid light guide 208, via coupler 206. The numerical aperture of the liquid light guide 208 is greater than that of the fiber 204 and thus no optics were needed to couple the fiber 204 to the liquid light guide 208. A Newport® lens 210 with a focal length of 25.4 mm was used at an approximate distance of 6 cm from the liquid light guide 208 to focus the beam 211. The diameter of the beam 211 when focused was approximately 1.2 cm.

A second option was investigated to couple the viewer to a camera and then view the fluorescing tissue on an external screen. A Sony® SC-75 CCD video camera module coupled with the FIND-R-SCOPE® and Pinnacle® software was used to view the fluorescing tissue on an external screen. This setup was also used to take pictures and video of the auto-fluorescence.

Tissue Fluorescence Comparison.

Finally the complete system as photographed in FIG. 3F was tested. A cage was built in front of the liquid light guide that created a simple reference to ensure that the light from the liquid light guide was properly focused. This excitation system was used to excite human tissue samples of thyroid and parathyroid. The auto-fluorescence of both the thyroid and the parathyroid were viewed using the viewer and pictures were taken using the camera/viewer-coupled system.

Power Needed for Minimum Detectability of Tissue Fluorescence.

Figure 4:
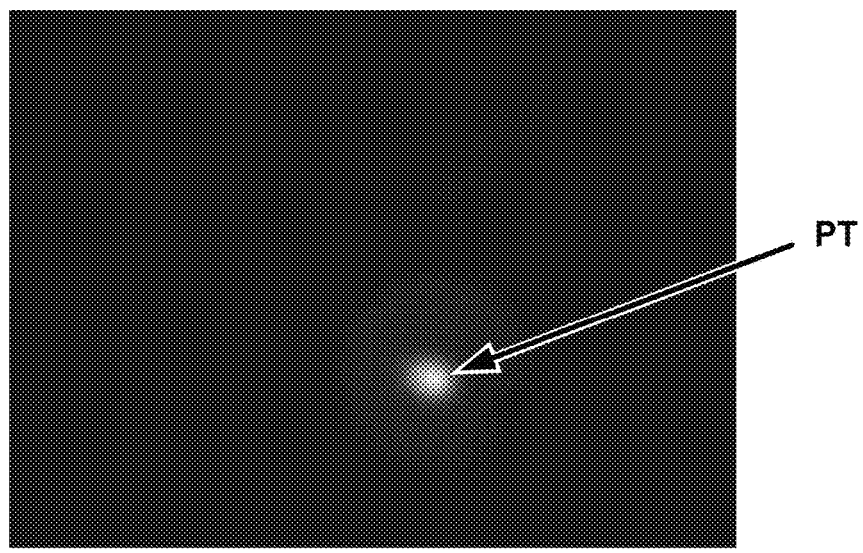
FIG. 4 shows an image of tissue taken with a viewer/camera coupled system according to one embodiment of the present invention.

The minimum power at which near-infrared light could be viewed using the viewer was determined to be 3 nW. The spectral resolution of the viewer/camera-coupled system was found to be 8 nW. FIG. 4 is a picture taken with the viewer/camera-coupled system, showing parathyroid tissue (PT).

Viewing Tissue Auto-Fluorescence.

The filter applied to the viewer blocked all wavelengths below 820 nm. Because the excitation laser used operates at a 785 nm, any light from the laser was blocked by the filter, and it cannot be seen. However, parathyroid auto-fluorescence, was still visible through the device. As stated previously, parathyroid tissue fluoresces at a much greater intensity than fat or thyroid tissue. The human eye cannot differentiate the parathyroid from surrounding tissue because the parathyroid fluoresces at a wavelength outside of the visible spectrum. This system would allow a surgeon to visually differentiate between tissue types based on auto-fluorescence within the NIR range.

Physical Specifications of the Device.

The system's small size and mobility make it adaptable for different operating room layouts and integratable with existing surgical equipment. The fact that it can be moved easily from place to place makes it cost-effective, as it reduces the need for the purchase of multiple viewing systems to be used by a single hospital.

Thus, a system according to one embodiment of the present invention as illustrated in Example 1 shows that by using the optical properties of the thyroid and parathyroid the system is able to visually differentiate the different tissue types during thyroid and parathyroid surgeries. This system when developed into a full surgical system can be installed into operating rooms. Improvements including increased spatial and spectral resolution for both the viewer and any secondary camera system, as well as a fully head mountable detector, viewer and excitation system can be made under the principle of the present invention. This system will help avoid injury/removal of the parathyroid as well as reduce surgical time and the need for secondary surgeries because the system will allow the surgeon to quickly and efficiently differentiate between surrounding tissue, thyroid and parathyroid. The visual cue will help the surgeon quickly differentiate between tissue types and possibly remove the need for sending tissue samples to histology during surgery when testing for accidental removal of parathyroid tissue. This will reduce time in surgery and will ensure that the correct tissue is removed avoiding post-operative hypoparathyroidism and eliminating the need for some secondary surgeries. Other possible improvements could include image processing to create a real time color map image of the fluorescent profile.

Example 2

This example in part illustrates a method or process, with corresponding apparatus or system, according to another embodiment of the present invention.

Referring now to FIG. 3C, a system 300C is schematically shown in a block diagram. The system 300C has a light source 302, which is designed to provide a beam of light with appropriate excitation wavelengths and energy so as to excite certain molecules of sample tissue 307, when receiving the beam of light, to generate auto-fluorescence emission. The system 300C also has a light delivery device 326, which is optically coupled with the light source 302 and delivers the beam of light from the light source 302 to the tissue 307. An optional filter 330 can be strategically positioned in an optical path 328 along which optical signals emitted from the tissue 307 responsive to the incident beam of light travel and utilized to reduce excess wavelengths and/or ambient light to ensure desirable optical signals to be detected. The system 300C further has a detector 333, which detects and records the optical signals emitted from the tissue 307. A lens 332 is positioned between the tissue 307 and the detector 333 to receive the optical signals emitted from the tissue and focus them on a desired spot on the detector 333. If an optional filter 330 is utilized, lens 332 will be positioned between the optional filter 330 and the detector 333. A computer 338, which has imaging display capacity or is associated with a display device, is at least in communication with the detector 333, where the computer 338 is adapted with appropriate controller cards and software to control signal acquisition, process data and display spectra, among other things. The display displays instant images processed by the computer 338 from the optical signals emitted from the tissue 307, which may guide a surgeon or a medical professional through a medical procedure to identify tissues and act on them accordingly.

FIG. 3D shows a photo of a system corresponding to system 300C of FIG. 3C, which was reduced to practice.

Imaging System and Measurements.

Detection using a probe-based NIR fluorescence system provided a fast and accurate way to detect parathyroid glands. This method is particularly useful when the parathyroid is located deep in the neck and is not necessarily exposed. However, in most cases, an imaging system would provide more spatial information to the surgeon improving upon the guidance using the probe based system. An NIR imaging setup was assembled to assess the feasibility of imaging the parathyroid. Tissue was excited with the same 785 nm diode laser, defocused to provide a ~6 cm diameter spot size. A notch filter was used to block reflected laser light. Images were obtained using a Aspherical HF 23-80 mm f/3.5-5.6 macro lens (Sigma, Ronkonkoma, N.Y.) with a PhotonMAX 512 (Princeton Instruments, Trenton, N.J.) charge-coupled device (CCD) camera. Images were recorded using Winview software (Princeton Instruments).

Figure 7:
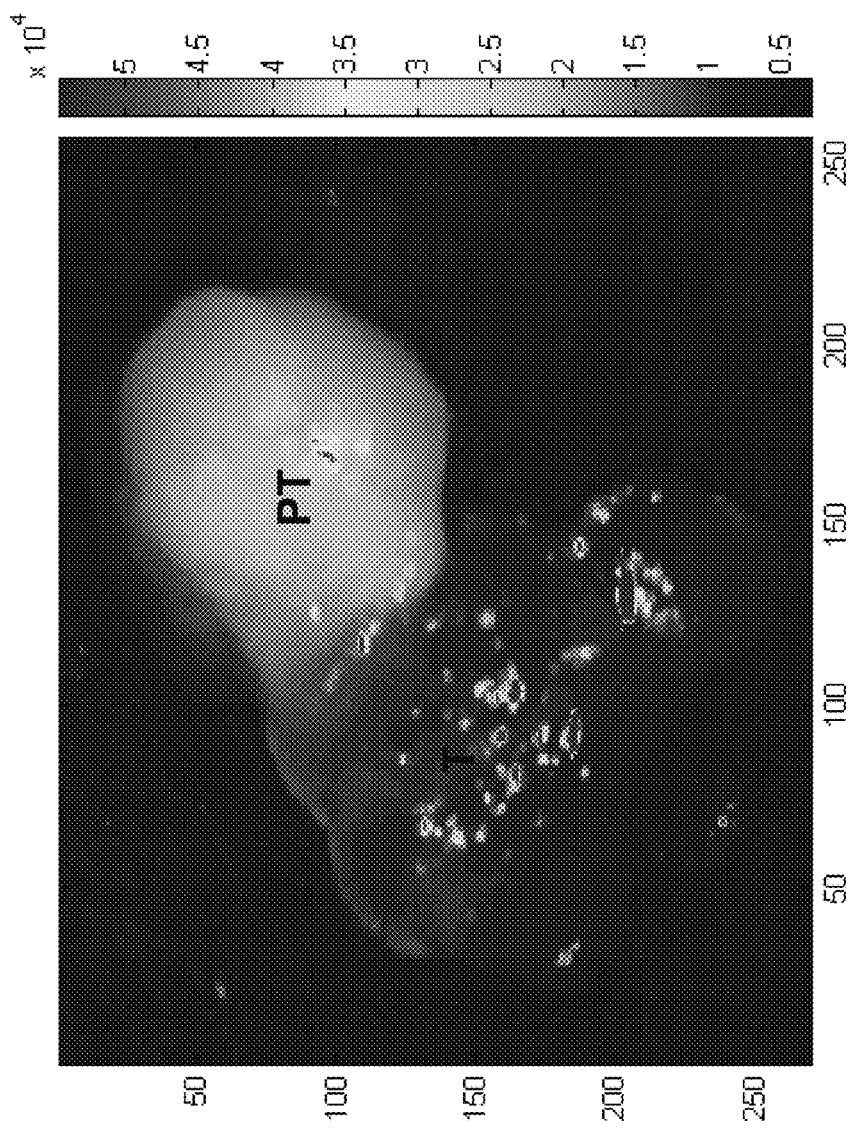
FIG. 7 shows in vitro auto-fluorescence of parathyroid and thyroid samples obtained from pathology all of which obtained through a method according to one embodiment of the present invention; as shown, the parathyroid (PT) located on the right exhibits at least two times stronger overall auto-fluorescence than the thyroid (T) located on the left.

Now referring also to FIG. 7, frozen samples of thyroid and parathyroid tissue were obtained and thawed and at room temperature in phosphate-buffered saline in a petri dish. A non-reflective, non-fluorescent layer was placed between the samples and the dish. The fluorescent room lights were turned off and the diode laser was used to illuminate both tissue samples equally. The light was delivered at a slight angle such that background specular reflection from the tissue was minimized. The camera was placed 7 inches above the tissues and focused. Images were taken with a 200 ms acquisition time using Winview. The images were processed using MATLAB to remove speckle by applying a median filter. FIG. 7 shows both glands fluorescing. The parathyroid is on the right and the thyroid on the left. The parathyroid fluoresces just over twice as much as the thyroid tissue. Not only was it possible to capture the intrinsic fluorescence with a camera but the parathyroid exhibits stronger auto-fluorescence in vitro as well as in vivo.

Thus, a system according to one embodiment of the present invention as illustrated in Example 2 shows that by using the optical properties of the thyroid and parathyroid the system is able to visually differentiate the different tissue types during thyroid and parathyroid surgeries. This system can be developed into a full surgical system that can be installed into operating rooms. This system will help avoid injury/removal of the parathyroid as well as reduce surgical time and the need for secondary surgeries because the system will allow the surgeon to quickly and efficiently differentiate between surrounding tissue, thyroid and parathyroid. The visual cue will help the surgeon quickly differentiate between tissue types and possibly remove the need for sending tissue samples to histology during surgery when testing for accidental removal of parathyroid tissue. This will reduce time in surgery and will ensure that the correct tissue is removed avoiding post-operative hypoparathyroidism and eliminating the need for some secondary surgeries. Other possible improvements could include image processing to create a real time color map image of the auto-fluorescence profile.

Example 3

This example in part illustrates an apparatus or system, which can be utilized to practice a method or process according to one embodiment of the present invention.

Referring now to FIG. 3A, a system 300A is schematically shown in block diagram. The system 300A has a light source 302, which is designed to provide a beam of light with appropriate excitation wavelengths and energy so as to excite certain molecules of sample tissue 307, when receiving the beam of light, to generate fluorescence emission. The system 300A also has a light delivery and collection device 306, which is optically coupled with the light source 302 and delivers the beam of light from the light source 302 to the tissue 307 and collects optical signals emitted from the tissue 307 responsive to the incident beam of light. An optional filter 310 can be utilized to reduce excess wavelengths and/or ambient light to ensure desirable optical signals to be detected. The system 300A further has a detector 314, which detects and records the optical signals emitted from the tissue. A computer 318 is at least in communication with the detector 314, where the computer 318 is adapted with appropriate controller cards and software to control signal acquisition, process data and display spectra, among other things.

FIG. 3B shows a photo of a system corresponding to system 300A of FIG. 3A, which was reduced to practice.

Auto-Fluorescence Measurements.

Now also referring to FIGS. 5 and 6, clinical measurements were performed. Twenty-one patients ages 18-99 regardless of race and gender were included in the study under informed written consent. All patients with primary thyroid or parathyroid pathophysiology undergoing thryoidectomy or parathyroidectomy were considered. An initial evaluation was conducted by the participating endocrine surgeon while seeing the patients at the Vanderbilt Clinic. Final eligibility was determined in the preoperative evaluation based on clinical condition and safety of the patient.

Figure 5A:
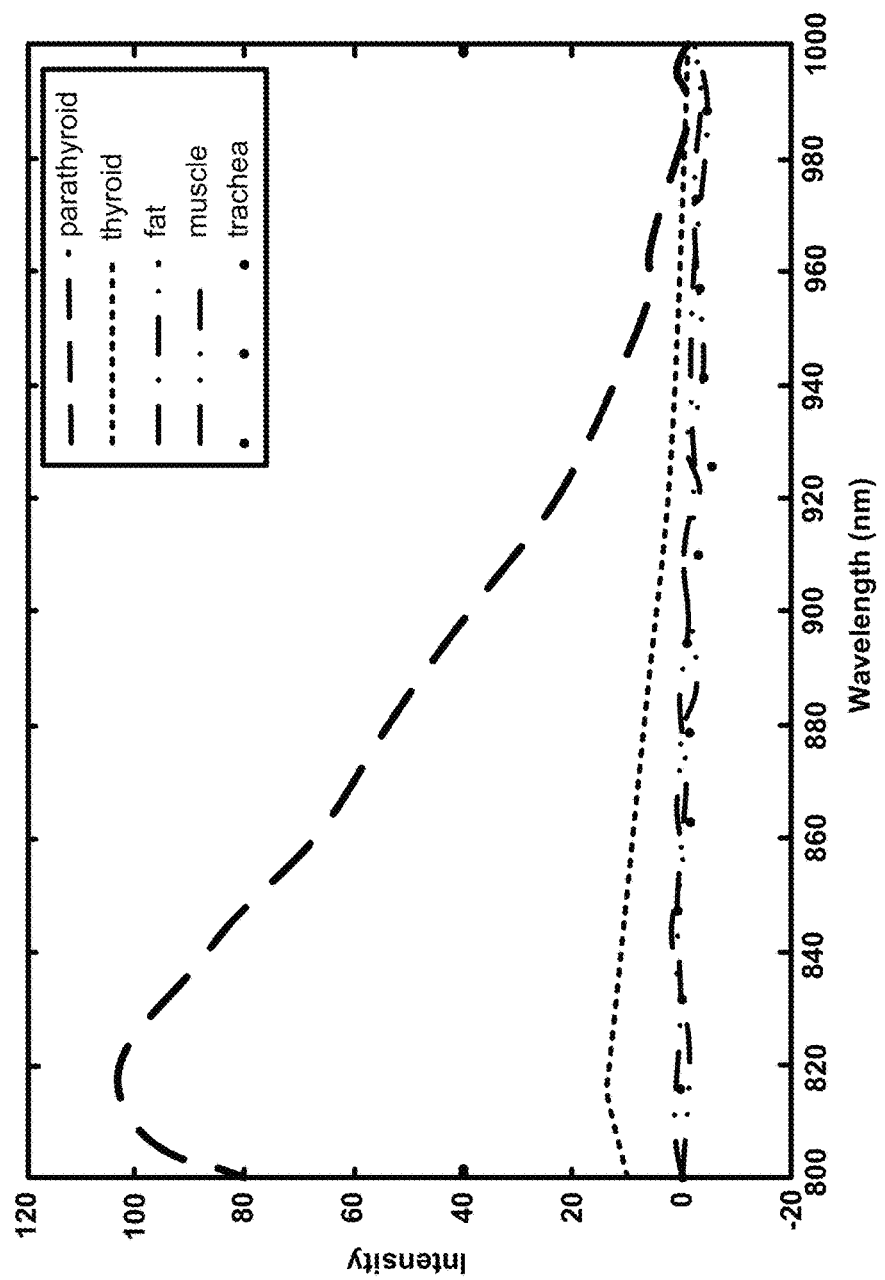
FIG. 5A shows near-infrared spectra obtained through a method according to one embodiment of the present invention, where the signal from each of the parathyroid, thyroid, fat, muscle, and trachea tissues are each represented by different respective dashed line pattern
Figure 5B:
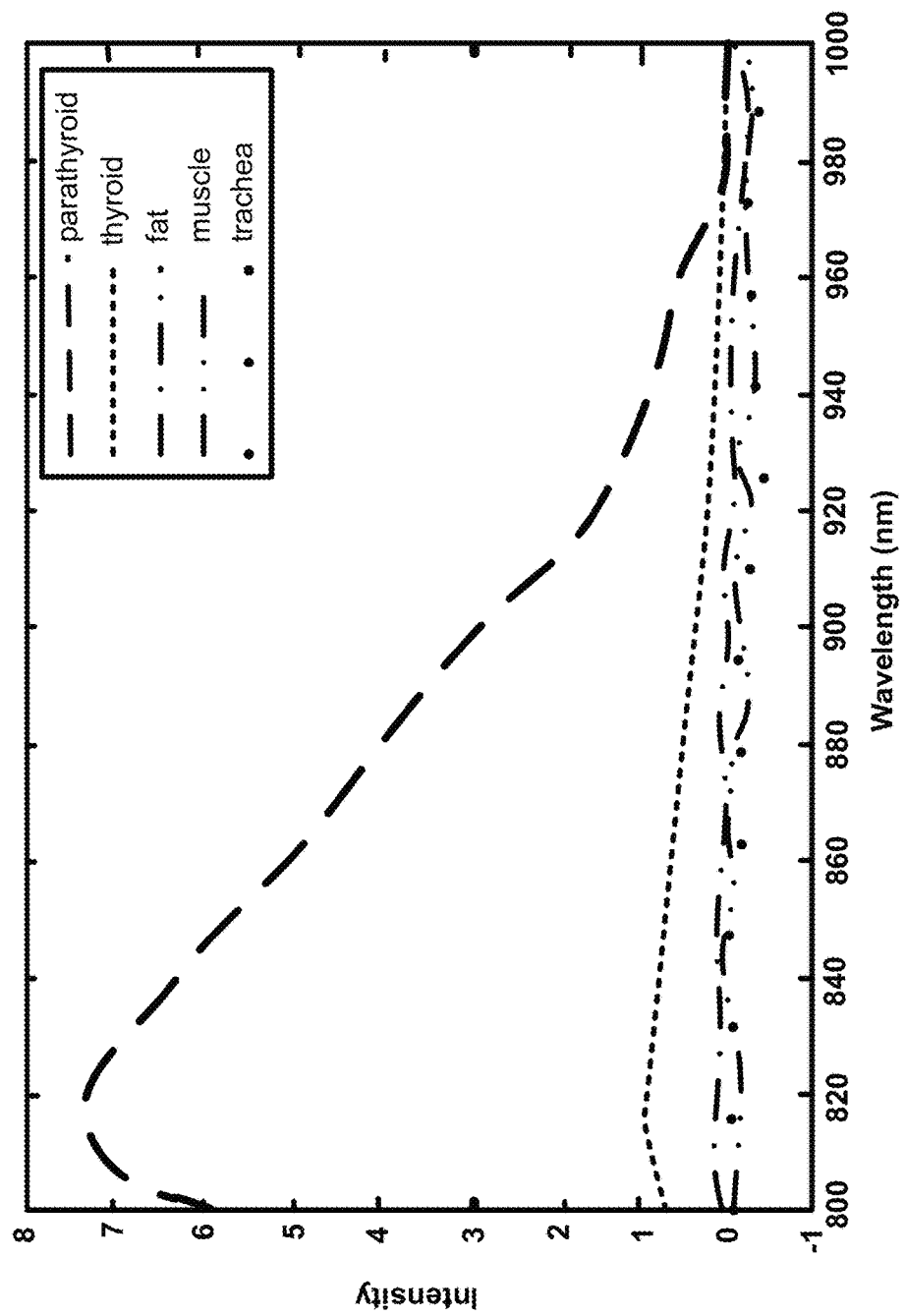
FIG. 5B shows near-infrared spectra in the form of a normalized signal obtained through a method according to one embodiment of the present invention from each of parathyroid, thyroid fat, muscle, and trachea tissues and each represented by a different respective dashed line pattern.
Figure 6A:
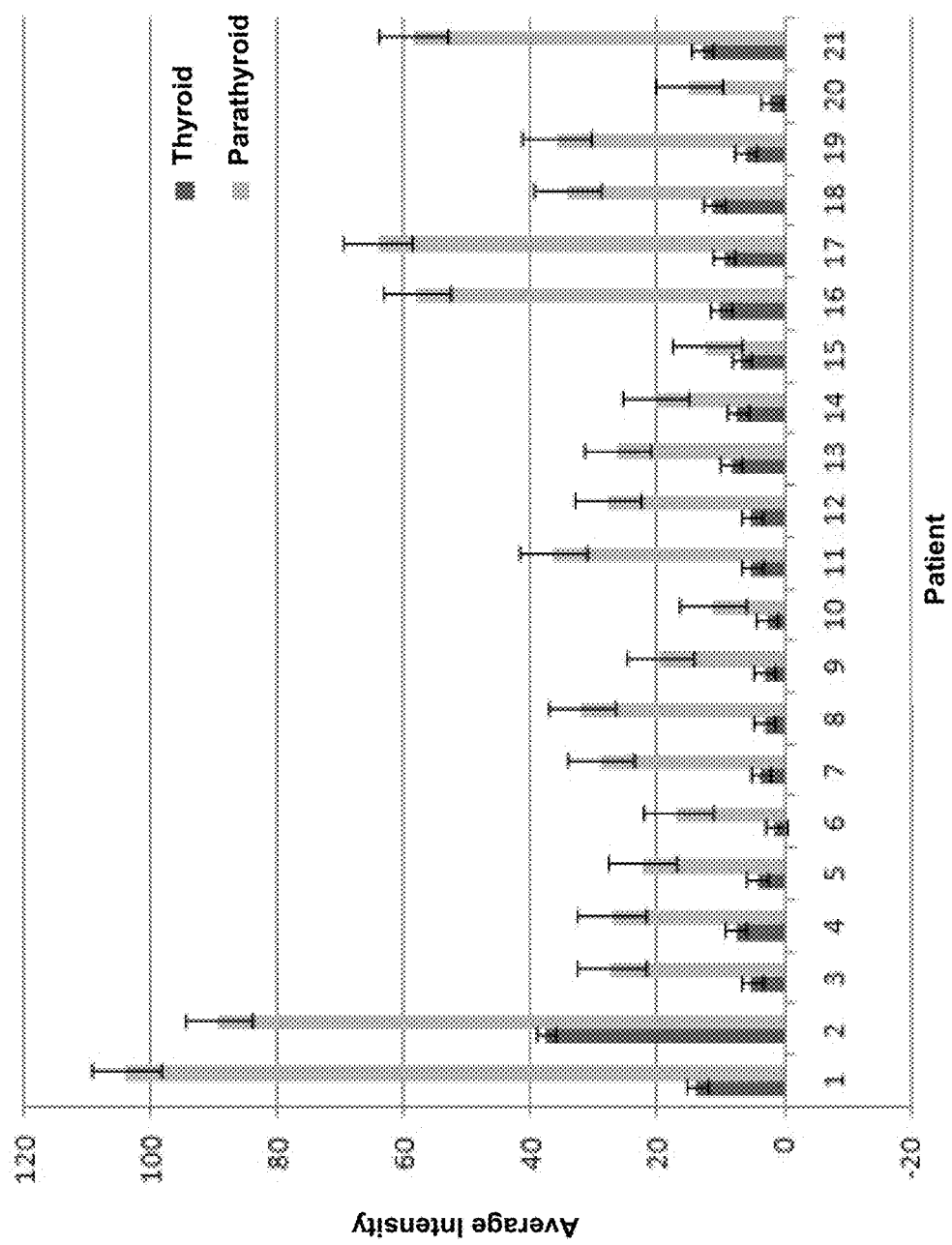
FIG. 6A shows average peak intensities of signals arising from parathyroid and thyroid measurements across 21 patients, as recorded by a near-infrared system according to one embodiment of the present invention; as shown, parathyroid tissue consistently exhibits a stronger signal than thyroid tissue.
Figure 6B:
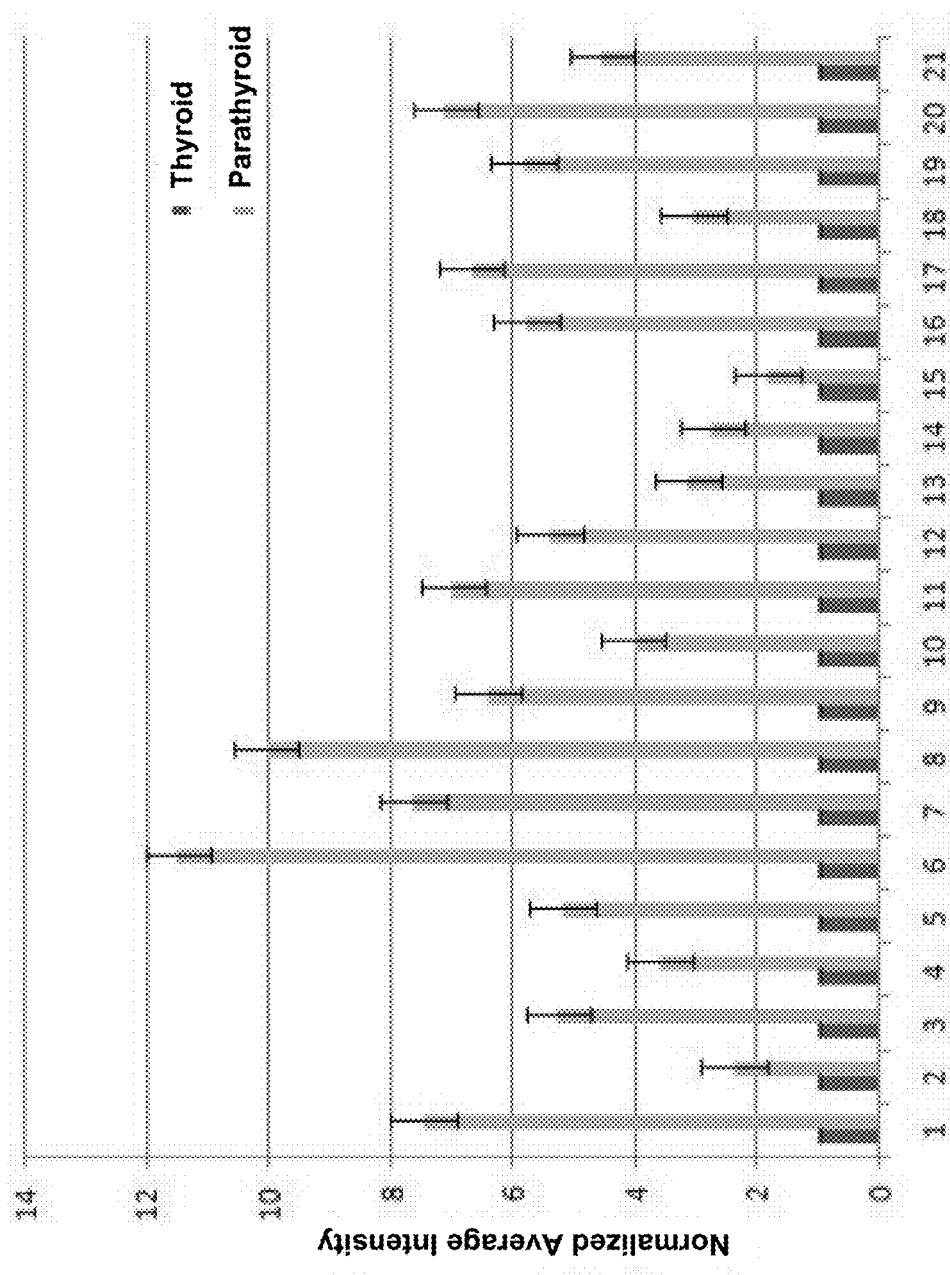
FIG. 6B shows normalized peak intensities of signals arising from parathyroid and thyroid measurements across 21 patients; as recorded by a near-infrared system according to ne embodiment of the present invention; each measurement is normalized to the average peak of all thyroid measurements.

A standardized protocol was followed for all fluorescence measurements from patients in vivo. During each surgery, the sterilized optical fiber probe was placed in contact with various tissues in the exposed neck area, and spectral measurements were acquired from each of those sites. The tissue type was noted, along with the physician's confidence in the investigated sites' histological identity. Spectra were collected using a 300 ms signal integration time. In all cases, the overhead fluorescent lights were turned off during the measurements, and other lights were turned away from the measurement site in case they contained spectral components that could interfere with the results. Any investigated sites that were surgically resected were collected for histological identification and analyzed by a pathologist. In each patient, the auto-fluorescence from the parathyroid was compared to the auto-fluorescence from the thyroid and other tissues in the neck. The signal from the parathyroid gland has the highest peak intensity and is easily distinguishable from the surrounding tissues as seen in FIGS. 5A and 5B, where auto-fluorescence spectra were obtained from light emitted from tissues in the neck area illuminated by a beam of light having a wavelength, each auto-fluorescence spectrum is corresponding to a type of tissues in the neck area, the wavelength is adapted such that the auto-fluorescence spectra of intensity of the light emitted from the illuminated tissues in the neck area are in a wavelength range of 800-1000 nm. As shown in FIGS. 5A and 5B, auto-fluorescence signal from each of the parathyroid, thyroid, fat, muscle, and trachea tissues are each represented by different respective dashed line pattern. Further, thyroid auto-fluorescence is stronger than surrounding muscle and fat but weaker than the parathyroid. Average peak intensity for parathyroid auto-fluorescence was consistently greater than that of the thyroid and other tissues with a p-value of 0.0001 across all patients shown in FIGS. 6A and 6B. Furthermore, parathyroid is 2-11 times more fluorescent than all other tissues found in the neck across all patients in vivo. Thus, the results from Example 3 are very promising. NIR auto-fluorescence provides an accurate detection of parathyroid tissue intra-operatively.

Statistical Analyses.

Clinical spectra were smoothed with an averaging filter of size 10. The 6 measurements from each site were average and then normalized to the mean peak thyroid intensity. A right-tailed student's T-test was used to test for the significance of the increased parathyroid signal over the 21 patients. Values of $P \leq 0.05$ were considered to be significant.

Understanding the Results.

The results set forth above show that NIR auto-fluorescence spectroscopy according to the present invention can successfully detect parathyroid tissue in vivo, in real-time and non-intrusively during endocrine surgery. In each patient, the parathyroid signal is greater than the signal from the thyroid and other tissues in the neck. Moreover, the p-value shows that the differences in signal strength are statistically significant and applicable across all patients and diseases. This finding is very promising for surgical identification. The system discriminates parathyroid glands from the surrounding tissue with high accuracy. Near-infrared auto-fluorescence is quick and relatively cheap to implement compared to other intraoperative localization methods such as a sestamibi scan, which can be very time consuming and expensive [1, 10, 11]. This method improves on the accuracy and sensitivity of visual recognition—a highly subjective measure dependent on the experience of the surgeon. Furthermore, most thyroidectomies and parathyroidectomies are typically performed by surgeons who do not perform a high volume of these surgeries, underscoring the clinical need for an improved method. Thus, the results from Example 3 are very promising. NIR auto-fluorescence provides an accurate detection of parathyroid tissue intra-operatively.

Example 4

This example in part illustrates an apparatus or system, which can be utilized to practice a method or process according to one embodiment of the present invention.

Figure 3G:
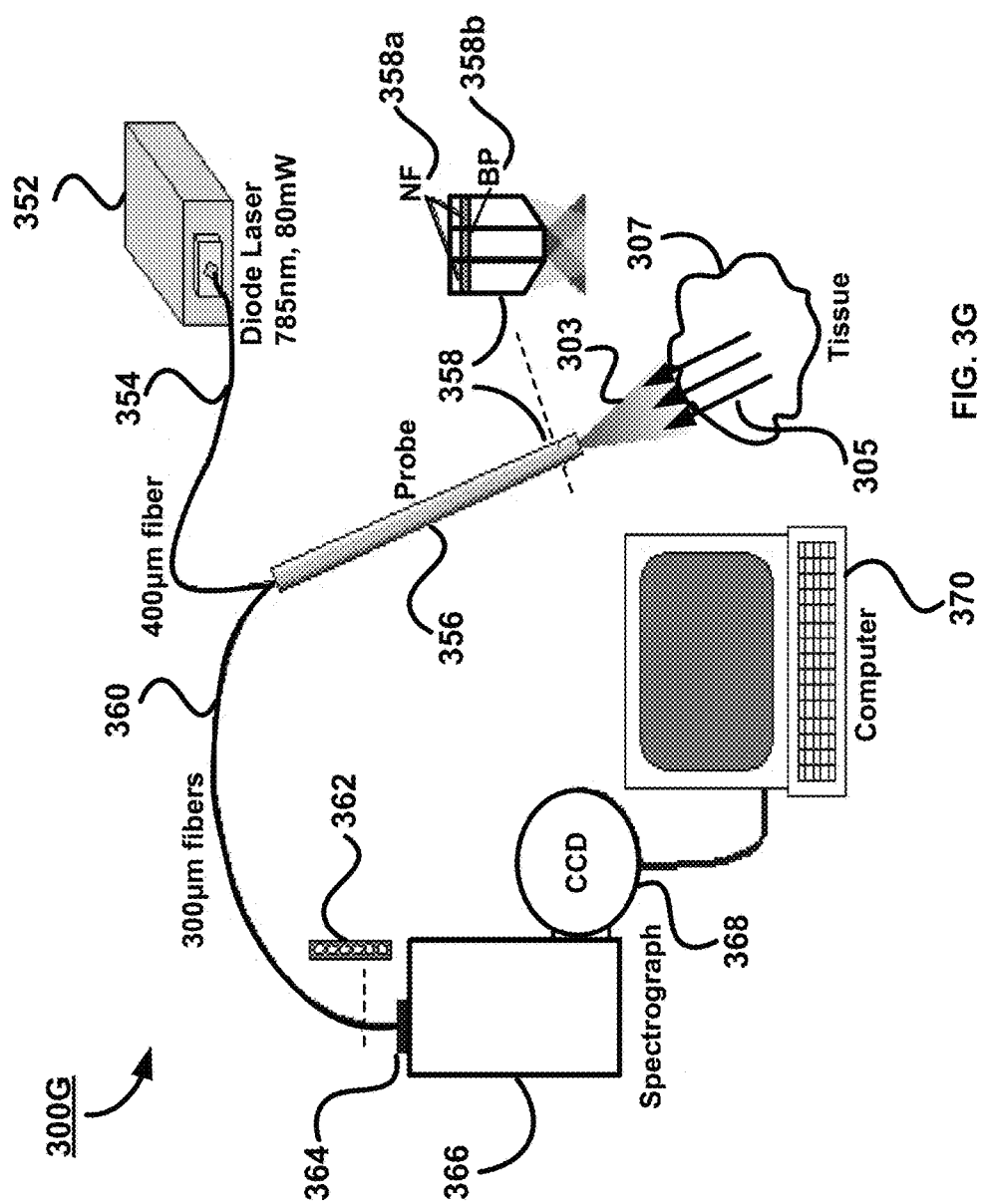
FIG. 3G schematically shows a system according to yet a further embodiment of the present invention.

Referring now to FIG. 3G, a system 300G is schematically shown. The system 300G has a light source 352, which is designed to provide a beam of light with appropriate excitation wavelengths and energy so as to excite certain molecules of sample tissue 307, when receiving the beam of light, to generate fluorescence emission. In this embodiment, the light source 352 is a diode laser capable of generating a beam of laser light with wavelength 785 nm and power 80 mW. Other suitable light sources can also be utilized to practice the present invention.

A first optical fiber 354 optically couples the light source 352 with a probe 356 that functions as a light delivery and collection device. In this embodiment, the first optical fiber 354 is a 300 µm fiber. The probe 356 receives a beam of light 303 from the light source 352 through the first optical fiber 354 and delivers it to the tissue 307 through head portion 358. The head portion 358 also collects optical signals 305 emitted from the tissue 307 responsive to the incident beam of light 303. In one embodiment, the head portion 358 is configured with a noise filter 358a and a band pass 358b to maintain the quality of the optical signals.

A second optical fiber 360 optically couples the probe 356 to means for recording, processing and displaying the optical signals, which, in one embodiment, includes a spectrograph 366, a CCD 368 and a computer 370 with display, where the CCD 368 is in communication with both spectrograph 366 and computer 370. The spectrograph 366 may have internal noise filter installed therein. The second optical fiber 360 is optically coupled with the spectrograph 366 through a coupler 364. Each of the first optical fiber 354 and the second optical fiber 360 may comprise one or more fibers. In one embodiment, the second optical fiber 360 has 6 or 7 of 300 µm fibers arranged in an array.

CCD 368 and computer 370, adapted with appropriate controller cards and software to control signal acquisition, process data and display spectra, are utilized to process and display images corresponding to the optical signals 305 emitted from the tissue 307, which may guide a surgeon or a medical professional through a medical procedure to identify tissues and act on them accordingly.

Figure 8:
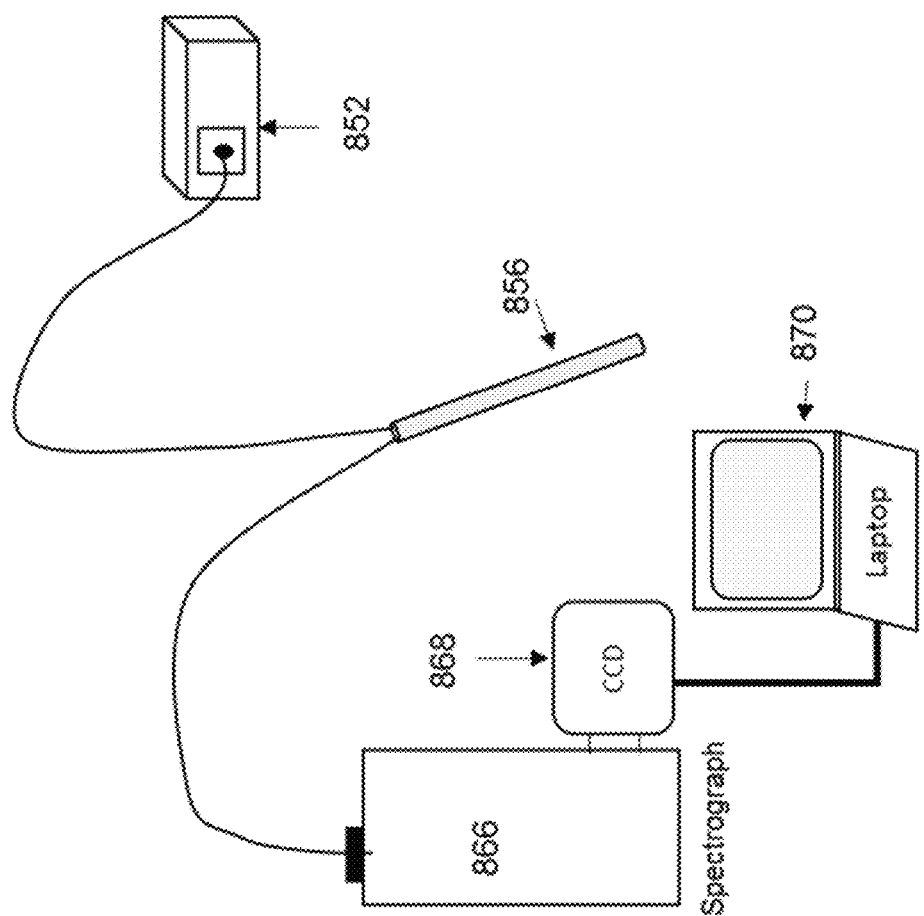
FIG. 8 is a photo of a clinical Raman system reduced to practice, which is corresponding to a system according to the embodiment of the present invention shown in FIG. 3G.
Figure 9:
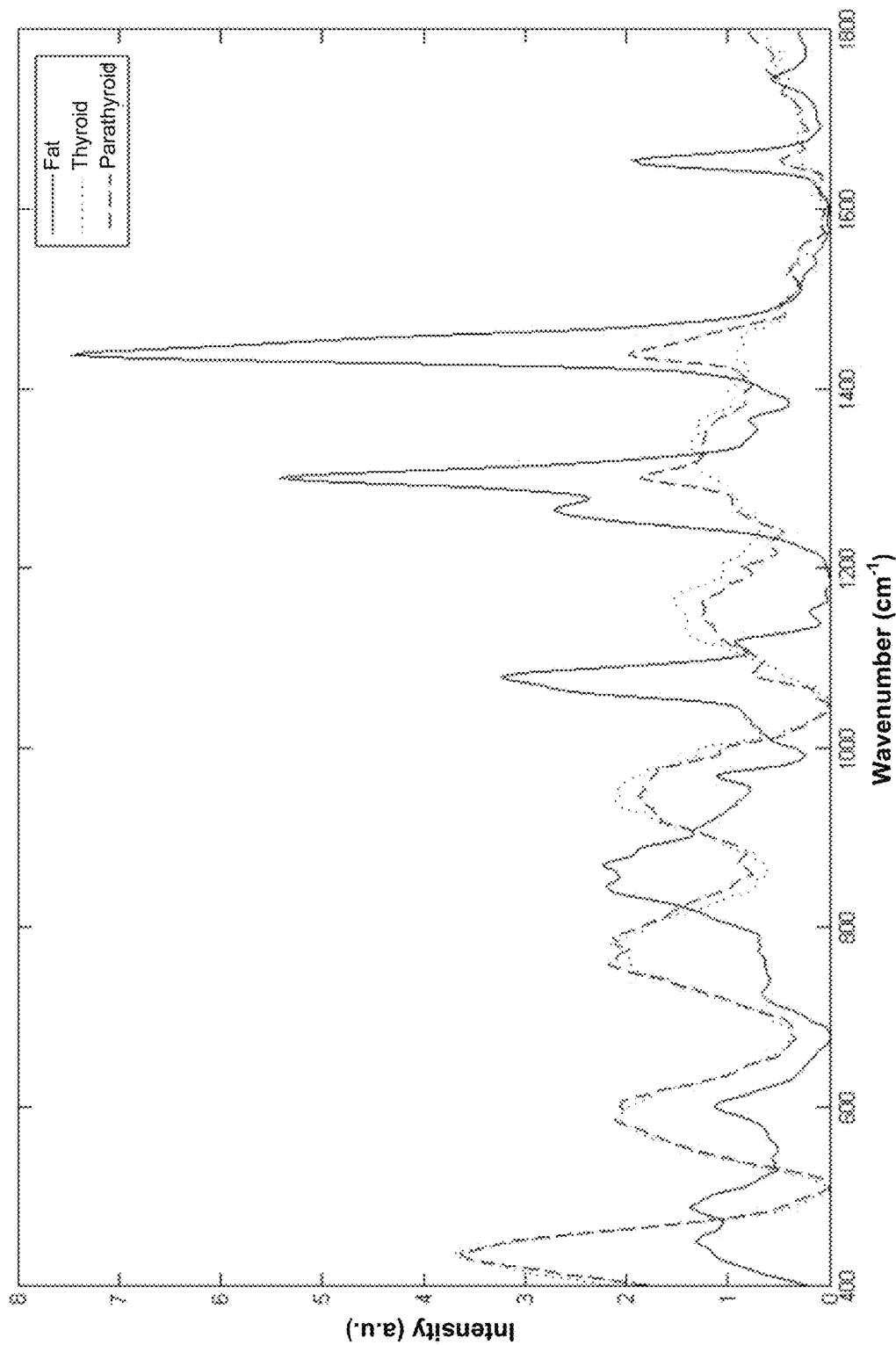
FIG. 9 shows processed Raman spectra of parathyroid tissue.

Now referring to FIGS. 8 and 9, FIG. 8 is a photo of a clinical Raman system reduced to practice, which is corresponding to system 300G of FIG. 3G. As previously discussed, Raman scattering is a very weak phenomena, and therefore practical measurement of Raman spectra of a medium requires high power excitation laser sources and extremely sensitive detection hardware. After detection, post processing techniques are required to subtract the fluorescence background and enable accurate visualization of the Raman spectra. FIG. 9 shows processed Raman spectra of various tissue types. As shown, Raman spectra are plotted as a function of frequency shift in units of wavenumber ($cm^{-1}$). The region of the Raman spectra where most biological molecules have Raman peaks is from 500 to 2000 $cm^{-1}$. In contrast to fluorescence spectra, Raman spectra have sharp spectral features that enable easier identification of the constituent sources of spectral peaks in a complex sample. In the context of detecting the changes that cancerous tissues undergo, differences in the Raman spectral features that correlate to the increased nucleic acid content in neoplastic cells has been observed.

Patients were recruited and an initial evaluation was conducted while seeing the patients at the Vanderbilt Clinic. Each patient's final eligibility for participating in the study was determined in the preoperative evaluation deeming the individual as a safe and acceptable candidate. Only adult patients between the ages of 18-99 years with primary thyroid or parathyroid pathophysiology undergoing thryoidectomy or parathyroidectomy were considered.

During the operations, the sterilized optical probe was placed on various tissues in the exposed neck area and spectral measurements were acquired from each of those sites. The tissue type was noted, as well as the physician's confidence in the investigated sites' histological identity. Spectra were collected using a 3 second signal collection time. If the signal saturated the fiber optic probe was kept in contact with the tissue and the signal collection time was reduced to 1 second. If saturation was observed at 1 second the signal collection time was again reduced to 0.1 second. In all cases, the overhead fluorescent lights were turned off during the measurements. Any luminescent lights left on were turned away from the measurement site. When medically appropriate, specimens from which measurements are taken were then collected for histological identification. All specimens collected were processed and analyzed by a pathologist.

For most samples, the raw spectra collected in vivo exhibited the distinct signal saturation in measurements of the parathyroid glands. The raw spectra from parathyroid samples saturated 35 times out of 40 measurements, or 87.5%. The signal saturated from the thyroid in only 17 of 49 measurements, or 34.7%. The signal from nerve, fat, and lymph node was not observed to have saturated. While the signal intensity varies slightly from measurement to measurement, on average the raw signal from the parathyroid is at least two times greater than that of the thyroid and the other surrounding tissues measured. This difference in intensity of the signals was seen immediately after the measurement was taken intraoperatively.

This study aimed to investigate if parathyroid tissue has unique optical properties that could be used to identify the parathyroid glands and differentiate them from neck background intraoperatively. We assessed the capabilities of Raman spectroscopy to accomplish this differentiation. Preliminary studies clearly indicated the potential for identifying the various tissues of the neck. Measurements taken of the tissue in the neck, including parathyroid, thyroid, lymph nodes, nerve, and fat, indicated these tissues have unique optical properties. The raw signal from parathyroid saturates while this was not observed as often in other tissues.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LIST OF REFERENCES

[1] Doherty, G. M. Thyroid and Parathyroid. in *Oncology* 992-1013 (2006).

[2] Bliss, R. D., Gauger, P. G. & Delbridge, L. W. Surgeon's approach to the thyroid gland: surgical anatomy and the importance of technique. *World journal of surgery* 24, 891-897 (2000).

[3] Miller, F. R. Surgical anatomy of the thyroid and parathyroid glands. *Otolaryngologic clinics of North America* 36, 1-7, vii (2003).

[4] ATA. Thyroid Surgery. (American Thyroid Association, 2005).

[5] Prosst, R. L., Gahlen, J., Schnuelle, P., Post, S. & Willeke, F. Fluorescence-guided minimally invasive parathyroidectomy: a novel surgical therapy for secondary hyperparathyroidism. *Am J Kidney Dis* 48, 327-331 (2006).

[6] Frilling, A. & Weber, F. Complications in Thyroid and Parathyroid Surgery. in *Surgery of the Thyroid and Parathyroid Glands* 217-224 (2007).

[7] Ahuja, A. T., et al. Imaging for primary hyperparathyroidism—what beginners should know. *Clinical radiology* 59, 967-976 (2004).

[8] Fakhran, S., Branstetter, B. F. t. & Pryma, D. A. Parathyroid imaging. *Neuroimaging clinics of North America* 18, 537-549, ix (2008).

[9] Ramanujam, N., et al. Spectroscopic diagnosis of cervical intraepithelial neoplasia (CIN) in vivo using laser-induced fluorescence spectra at multiple excitation wavelengths. *Lasers in surgery and medicine* 19, 63-74 (1996).

[10] Lakowicz, J. R. Fluorophores. in *Principles of Fluorescence Spectroscopy* 63-95 (2006).

[11] Kim, L. a. A. M. Hyperparathyroidism. (ed. Daniel Einhorn, F. T., Don S Schalch, Mark Cooper and George T Griffing) (Webmd, 2008).

[12] Lakowicz, J. R. Introduction to Fluorescence. in *Principles of Fluorescence Spectroscopy* 1-26 (2006).

[13] Monici M., Cell and tissue autofluorescence research and diagnostic applications. *Biotechnol Annu Rev.* 11:227-56 (2005).

What is claimed is:

1. A process for intra-operatively identifying a parathyroid tissue of a living subject, comprising the steps of:
   (a) illuminating, with a light, source, tissues in the neck area of the living subject with a beam of light having a predetermined wavelength;
   (b) obtaining, with a detector, auto-fluorescence spectra of intensity from light emitted from the illuminated tissues in the neck area, wherein each auto-fluorescence spectrum is corresponding to a region of the neck area whose tissue emits auto-fluorescence light in response to the illumination, wherein the predetermined wavelength is adapted such that the auto-fluorescence spectra of intensity of the light emitted from the illuminated tissues in the neck area are in a wavelength range of 800-1000 nm;
   (c) identifying, with a controller, one of the auto-fluorescence spectra having a highest peak intensity among the auto-fluorescence spectra; and
   (d) identifying, with the controller, the tissue of the region of the neck area that corresponds to the one of the auto-fluorescence spectra having the highest peak intensity as the parathyroid tissue.

2. The process of claim 1, wherein the predetermined wavelength is in the near-infrared range.

3. The process of claim 2, wherein the predetermined wavelength is about 785 nm.

4. The process of claim 1, wherein the step of obtaining the auto-fluorescence spectra of intensity comprises collecting the light emitted from the illuminated tissues with a collection probe and obtaining the auto-fluorescence spectra with a fluorescence spectrometer.

5. The process of claim 1, further comprising the steps of identifying another one of the auto-fluorescence spectra having a peak intensity that is less than the highest peak intensity but greater than other peak intensities among the auto-fluorescence spectra and identifying the tissue of the region of the neck area that corresponds to the another one of the auto-fluorescence spectra having the peak intensity as a thyroid tissue.

6. The process of claim 5, further comprising the step of displaying images visually representing the auto-fluorescence spectra in real time to a medical professional performing an endocrine surgery.

7. The process of claim 1, wherein the step of finding the highest peak intensity in the auto-fluorescence spectrum comprises finding the highest peak intensity in the auto-fluorescence spectrum at a wavelength of about 822 nm.

8. A system for intra-operatively identifying a parathyroid tissue of a living subject, comprising:
   (a) a light source configured to emit a beam of light having a wavelength for illuminating tissues in the neck area of the living subject;
   (b) means for collecting light emitted from the illuminated tissues in response to the illumination;

(c) means for obtaining auto-fluorescence spectra of intensity from the collected light emitted from the illuminated tissues in the neck area, wherein each auto-fluorescence spectrum is corresponding to a region of the neck area whose tissue emits auto-fluorescence light in response to the illumination, wherein the wavelength is adapted such that the auto-fluorescence spectra of intensity of the light emitted from the illuminated tissues in the neck area are in a wavelength range of 800-1000 nm;

(d) means for finding one of the auto-fluorescence spectra having a highest peak among the auto-fluorescence spectra; and (e) means for identifying a tissue of the region of the neck area that corresponds to the one of the auto-fluorescence spectra having the highest peak as the parathyroid tissue.

9. The system of claim 8, wherein the wavelength is in the near-infrared range.

10. The system of claim 9, further comprising an optical fiber means optically coupled to the light source, for receiving the beam of light from the light source and delivering the received beam of light to the tissues.

11. The system of claim 8, wherein the means for obtaining the auto-fluorescence spectra of intensity comprises a collection probe and a fluorescence spectrometer.

12. The system of claim 8, further comprising a means for displaying real-time images visually representing the auto-fluorescence spectra to a medical professional performing an endocrine surgical procedure.

13. A process for intra-operatively providing anatomical guidance in endocrine surgery, comprising the steps of:

(a) illuminating, with a light source, tissues in the neck area of a living subject with a beam of light having a predetermined wavelength;

(b) obtaining, with a detector, auto-fluorescence spectra of intensity from light emitted from the illuminated tissues in the neck area, wherein each auto-fluorescence spectrum is corresponding to a region of the neck area whose tissue emits auto-fluorescence light in response to the illumination, wherein the predetermined wavelength is adapted such that the auto-fluorescence spectra of intensity of the light emitted from the illuminated tissues in the neck area are in a wavelength range of 800-1000 nm;

(c) identifying, with a controller, one of the auto-fluorescence spectra having a highest peak intensity among the auto-fluorescence spectra;

(d) identifying, with the controller, the tissue of the region of the neck area that corresponds to the one of the auto-fluorescence spectra having the highest peak intensity as the parathyroid tissue; and (e) displaying images of the obtained auto-fluorescence data on a display for providing anatomical guidance to a medical professional performing the endocrine surgery.

14. The process of claim 13, wherein the predetermined wavelength is in the near-infrared range.

15. The process of claim 13, wherein the auto-fluorescence data comprises near-infrared auto-fluorescence data.

16. A system for intra-operatively providing anatomical guidance in an endocrine surgery, comprising:

(a) a light source configured to emit a beam of light having a wavelength for illuminating tissues in the neck area of a living subject with the beam of light;

(b) means for obtaining auto-fluorescence spectra of intensity from light emitted from the illuminated tissues in the neck area, wherein each auto-fluorescence spectrum is corresponding to a region of the neck area whose tissue emits auto-fluorescence light in response to the illumination, wherein the wavelength is adapted such that the auto-fluorescence spectra of intensity of the light emitted from the illuminated tissues in the neck area are in a wavelength range of 800-1000 nm;

(c) means for finding one of the auto-fluorescence spectra having a highest peak among the auto-fluorescence spectra;

(d) means for identifying a tissue of the region of the neck area that corresponds to the one of the auto-fluorescence spectra having the highest peak as the parathyroid tissue; and (e) a display in communication with the means for obtaining auto-fluorescence data and configured to display images generated from the obtained auto-fluorescence data, for providing anatomical guidance in an endocrine surgery.

17. The system of claim 16, wherein the light source comprises a laser configured to emit the beam of light having a wavelength in the near-infrared range.

18. A process for intra-operatively identifying thyroid or parathyroid cells of a living subject, comprising the steps of:

(a) illuminating, with a light source, tissues in the neck area of the living subject with a beam of light having a wavelength;

(b) obtaining, with a detector, auto-fluorescence spectra of intensity from light emitted from the illuminated tissues in the neck area, wherein each auto-fluorescence spectrum is corresponding to a region of the neck area whose tissue emits auto-fluorescence light in response to the illumination, wherein the wavelength is adapted such that the auto-fluorescence spectra of intensity of the light emitted from the illuminated tissues in the neck area are in a wavelength of 800-1000 nm;

(c) identifying, with a controller, one of the auto-fluorescence spectra having a peak intensity among the auto-fluorescence spectra; and (d) identifying, with the controller, cells in the tissue of the region of the neck area that corresponds to the one of the auto-fluorescence spectra having the highest peak intensity as the parathyroid cells.

19. The process of claim 18, wherein the illuminating step comprises the step of illuminating the tissues with the beam of light from a near-infrared light source.

20. The process of claim 18, wherein the step of obtaining the auto-fluorescence spectra comprises collecting the emitted light in a collection probe and obtaining the auto-fluorescence spectra with a fluorescence spectrometer.

21. The process of claim 18, further comprising the step of displaying images visually representing the auto-fluorescence spectra in a display for guiding a medical professional through an endocrine surgery.

22. A system for intra-operatively identifying thyroid or parathyroid cells of a living subject, comprising:

(a) a light source configured to emit a beam of light having a wavelength for illuminating tissues in the neck area of the living subject;

(b) an optical probe for collecting light emitted from the illuminated tissues;

(c) means for obtaining auto-fluorescence spectra of intensity from the collected light emitted from the illuminated tissues in the neck area, wherein each auto-fluorescence spectrum is corresponding to a region of the neck area whose tissue emits auto-fluorescence light in response to the illumination, wherein the wavelength is adapted such that the auto-fluorescence spectra of intensity of the light emitted from the illuminated tissues in the neck area are in a wavelength range of 800-1000 nm;
(d) means for identifying one of the auto-fluorescence spectra having a peak intensity among the auto-fluorescence spectra;
(e) means for comparing the one of the auto-fluorescence spectra having a peak intensity to a baseline spectrum; and
(f) means for identifying the presence of parathyroid cells as the highest peak intensity in the one of the auto-fluorescence spectra.

23. The system of claim 22, wherein the light source comprises a near-infrared laser.

24. The system of claim 22, further comprising optical fiber means optically coupled to the light source, for receiving a beam of light from the light source and delivering the received beam of light to the tissues in the neck area of the living subject.

25. The system of claim 22, wherein the means for obtaining the auto-fluorescence spectrum comprises a fluorescence spectrometer.

26. The system of claim 25, further comprising a controller in communication with the fluorescence spectrometer and programmed for comparing a baseline auto-fluorescence spectrum of non-fluorescent tissues to the obtained auto-fluorescence spectra, and identifying the presence of thyroid or parathyroid cells from the comparison, and displaying images visually representing the auto-fluorescence spectra for guiding a medical professional through an endocrine surgery.

* * * * *